United States Patent
Williamson

(10) Patent No.: US 12,383,133 B2
(45) Date of Patent: Aug. 12, 2025

(54) OPTICAL SYSTEM FOR CONVERTIBLE IMAGING OF POSTERIOR AND ANTERIOR PORTIONS OF THE EYE

(71) Applicant: NIKON CORPORATION, Tokyo (JP)

(72) Inventor: David M. Williamson, Tucson, AZ (US)

(73) Assignee: NIKON CORPORATION, Tokyo (JP)

( * ) Notice: Subject to any disclaimer, the term of this patent is extended or adjusted under 35 U.S.C. 154(b) by 639 days.

(21) Appl. No.: 17/549,306

(22) Filed: Dec. 13, 2021

(65) Prior Publication Data

US 2022/0095912 A1  Mar. 31, 2022

Related U.S. Application Data

(63) Continuation of application No. PCT/JP2020/023275, filed on Jun. 12, 2020.

(60) Provisional application No. 62/861,713, filed on Jun. 14, 2019.

(51) Int. Cl.
*A61B 3/12* (2006.01)
*A61B 3/00* (2006.01)
*G02B 13/00* (2006.01)

(52) U.S. Cl.
CPC .............. *A61B 3/12* (2013.01); *A61B 3/0025* (2013.01); *G02B 13/0095* (2013.01)

(58) Field of Classification Search
CPC ...... A61B 3/12; A61B 3/0025; G02B 13/0095
USPC ......................................................... 351/206
See application file for complete search history.

(56) References Cited

U.S. PATENT DOCUMENTS

| | | | |
|---|---|---|---|
| 2,235,319 | A | 3/1941 | Jobe |
| 4,222,634 | A | 9/1980 | Muchel |
| 4,592,625 | A | 6/1986 | Uehara et al. |
| 4,627,694 | A | 12/1986 | Volk |
| 4,738,521 | A | 4/1988 | Volk |
| 2001/0041884 | A1 | 11/2001 | Frey et al. |
| 2011/0080562 | A1 | 4/2011 | Iizuka et al. |
| 2012/0320340 | A1 | 12/2012 | Coleman, III |
| 2019/0261853 | A1 | 8/2019 | Williamson |

FOREIGN PATENT DOCUMENTS

| | | |
|---|---|---|
| CN | 204542052 U | 8/2015 |
| JP | S60-203233 A | 10/1985 |
| JP | 2003-019118 A | 1/2003 |
| JP | 2004-081387 A | 3/2004 |

(Continued)

*Primary Examiner* — Wyatt A Stoffa
*Assistant Examiner* — Grant A Gagnon
(74) *Attorney, Agent, or Firm* — Foley & Lardner LLP

(57) ABSTRACT

An reconfigurable optical arrangement for imaging posterior and anterior surfaces of a visual system. The optical arrangement includes a relay containing first and second lenses each having a positive optical power and detachably cooperated with one another such that the first lens and the second lens form an afocal system configured to form a conjugate relationship between the first plane and the second plane. In a related embodiment, the optical arrangement may include a first lens system of an first optical system housed in a body of a mobile telecommunication device and an afocal relay including first and second lenses that possess equal optical properties. Here, the afocal relay is configured to have a unity magnification and to provide diffraction-limited imaging within a spectral range from at least 486 nm to at least 656 nm. The method for imaging with the use of the optical arrangement.

6 Claims, 21 Drawing Sheets

(56) References Cited

FOREIGN PATENT DOCUMENTS

| JP | 2008-197190 A | 8/2008 |
|----|---------------|--------|
| WO | WO-2015/071779 A1 | 5/2015 |
| WO | WO-2018/043657 A1 | 3/2018 |

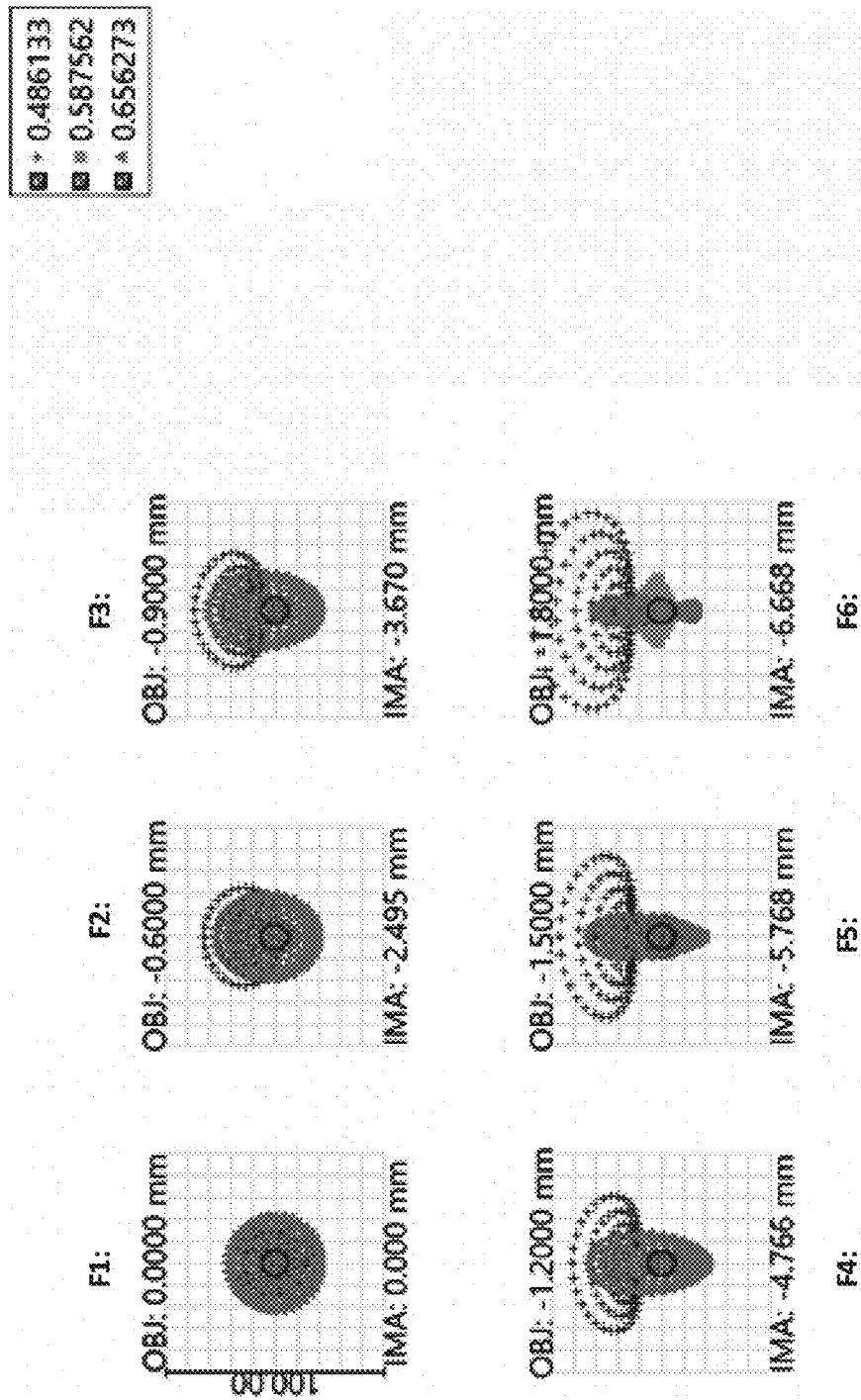

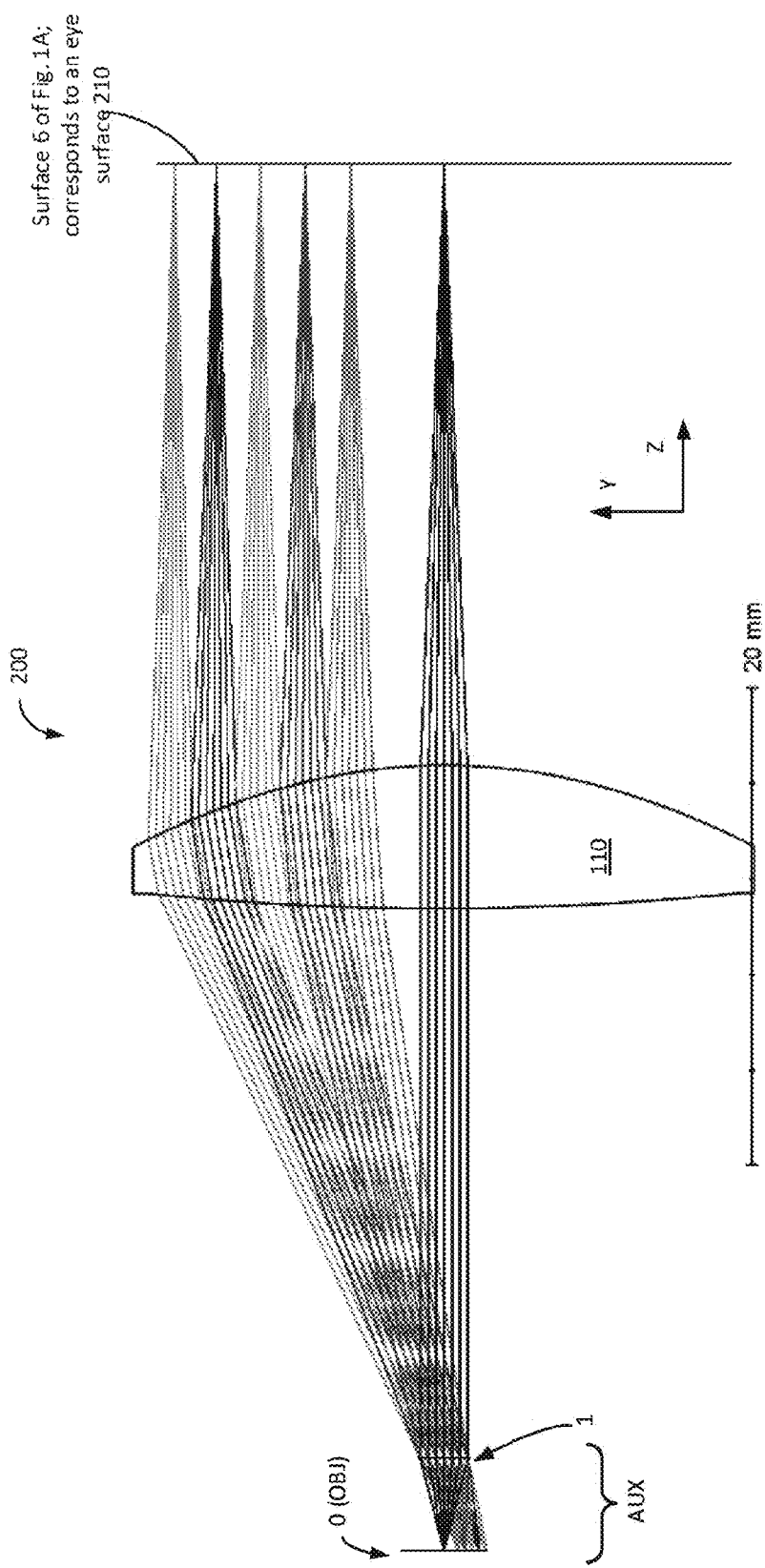

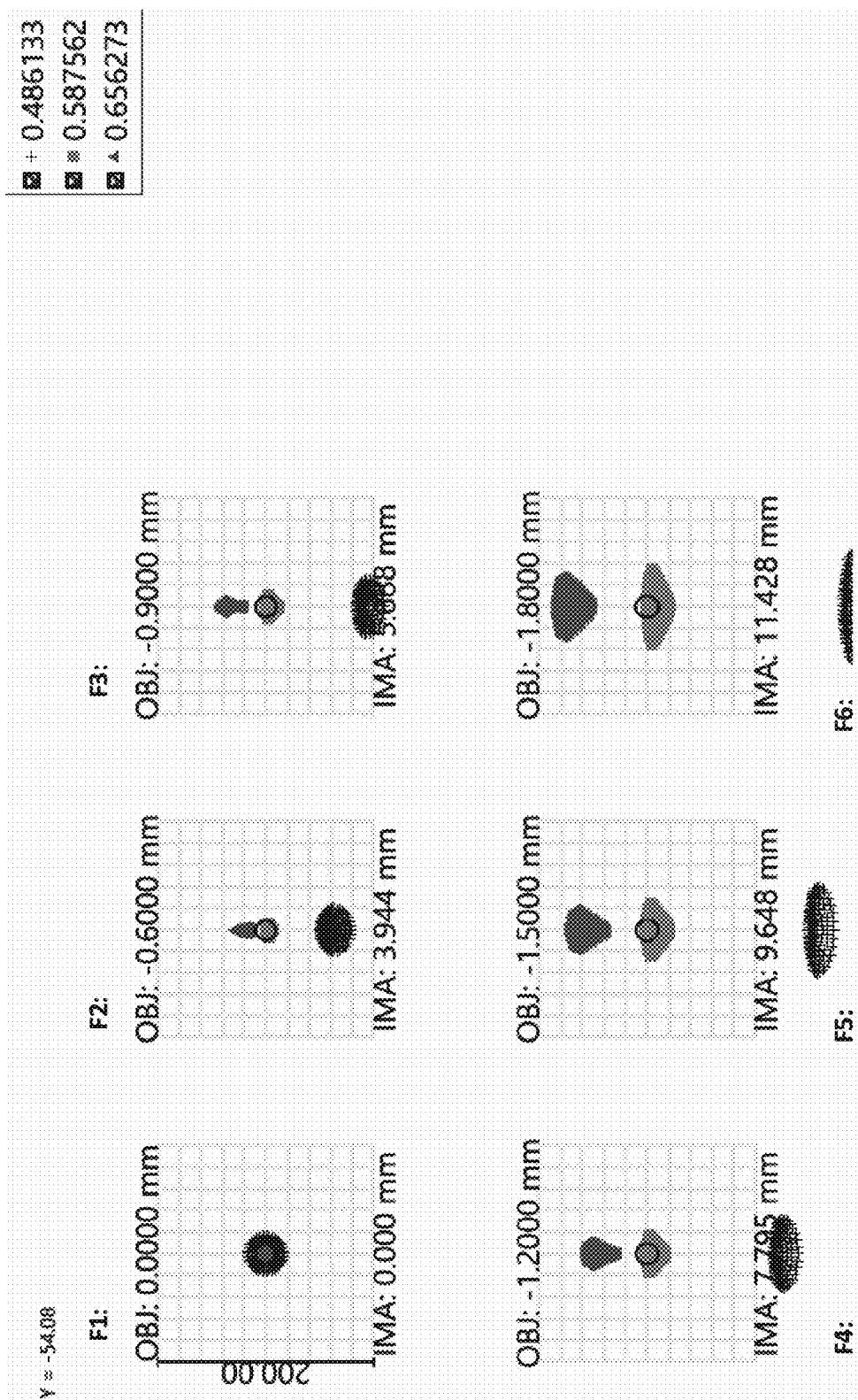

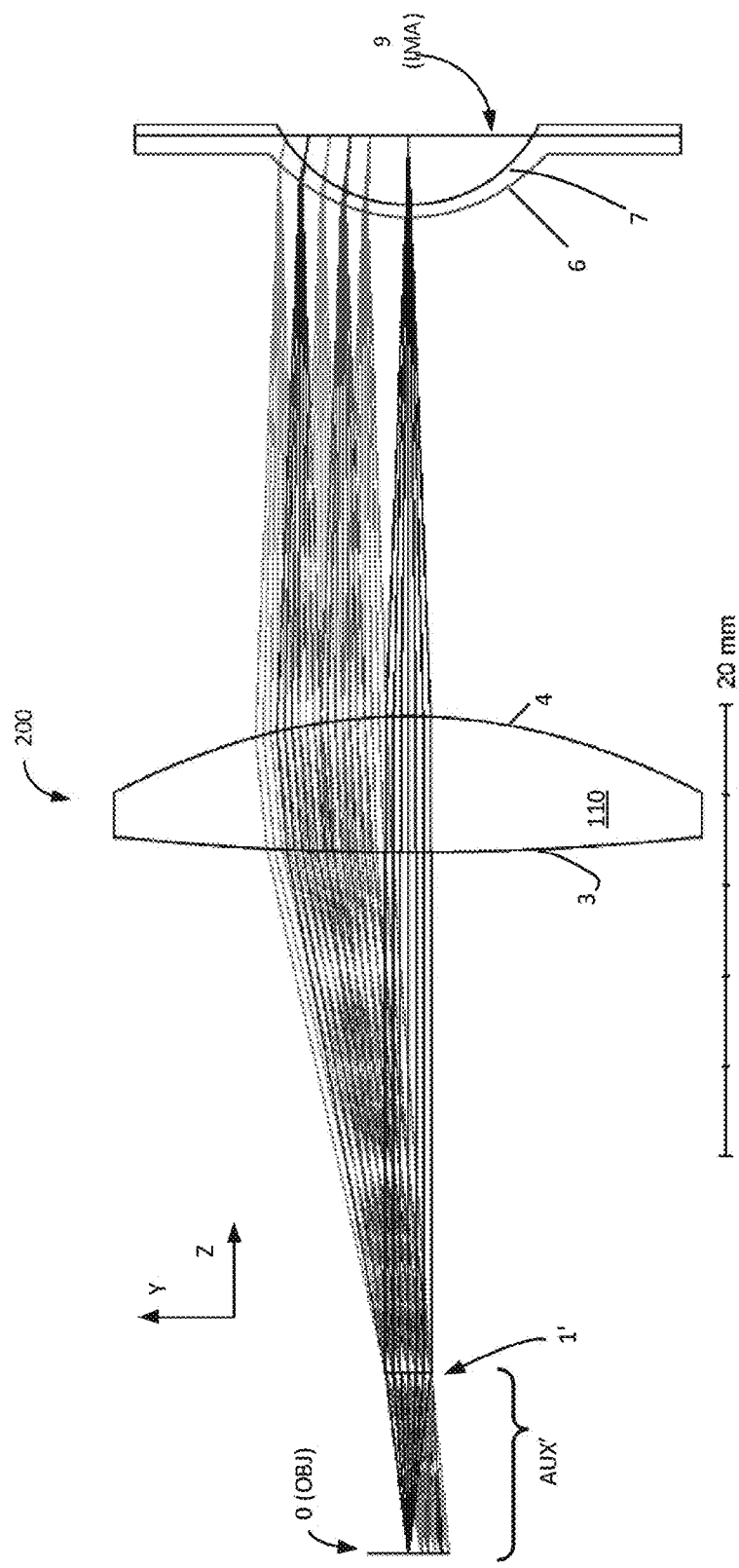

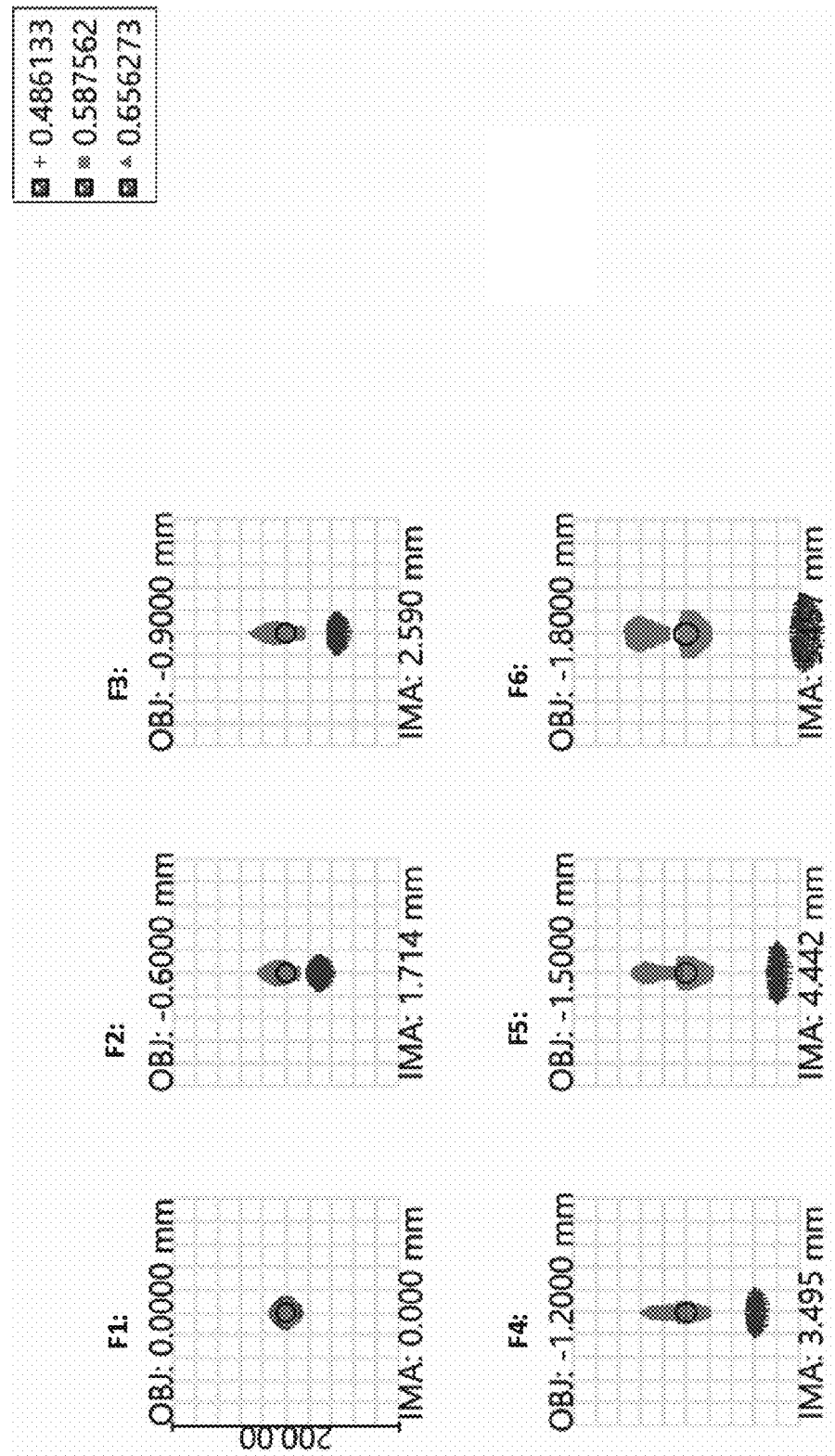

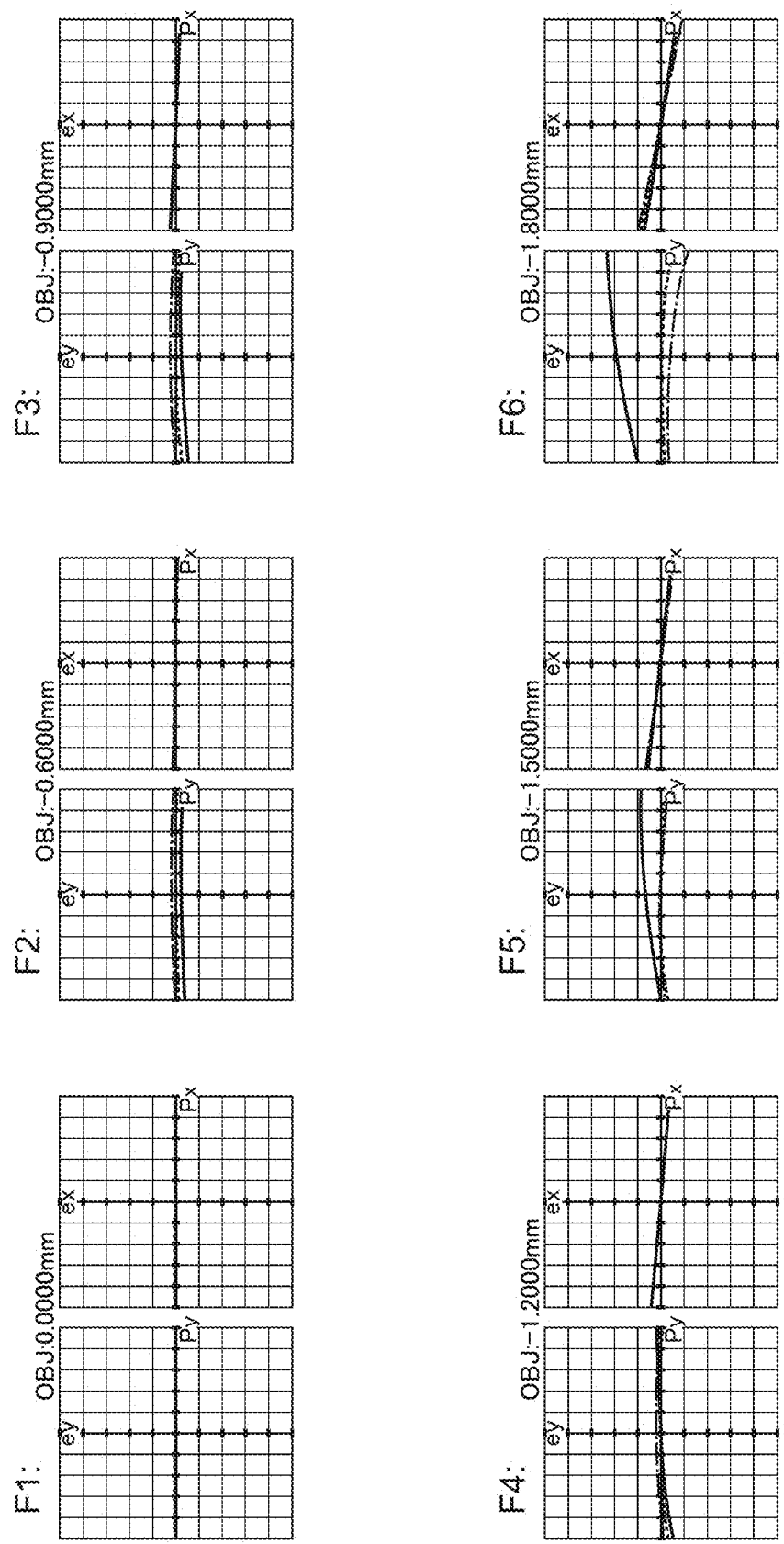

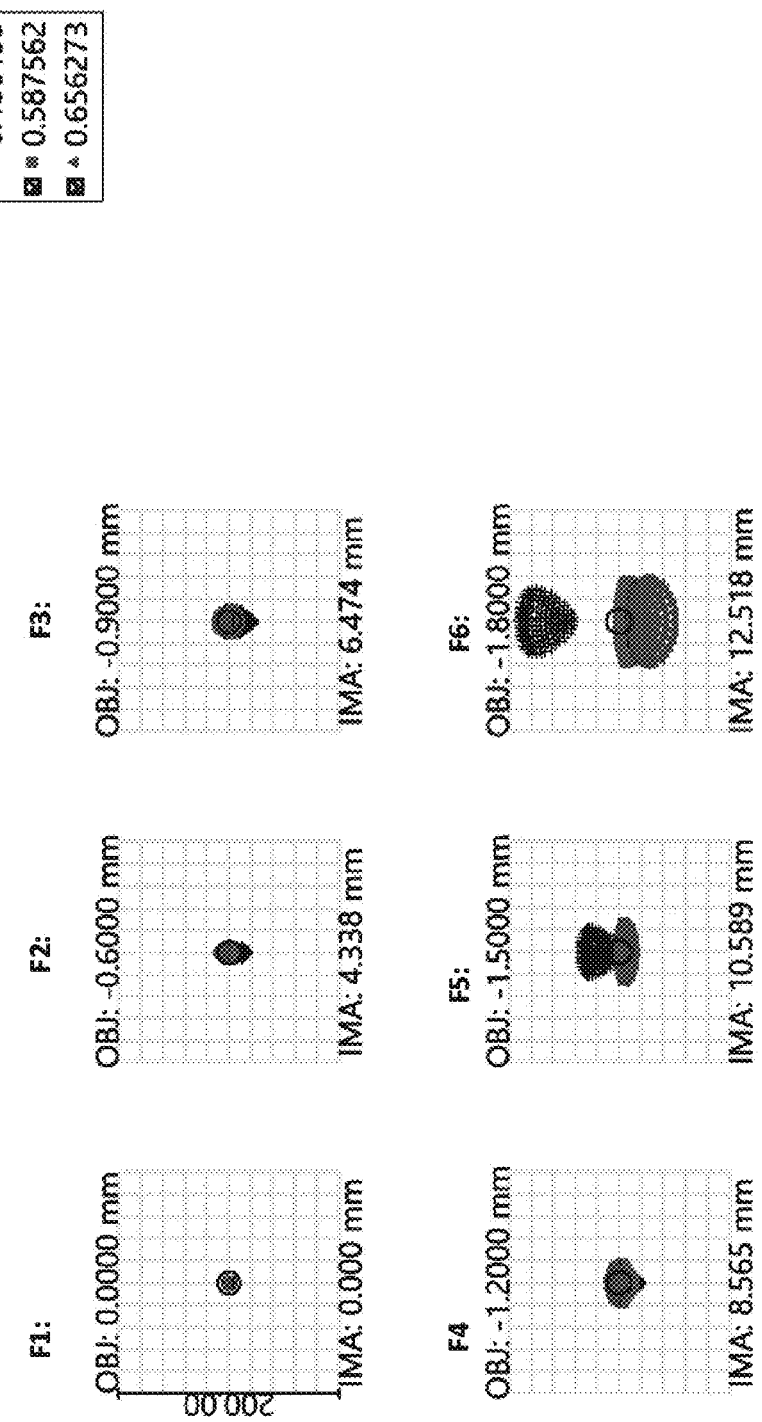

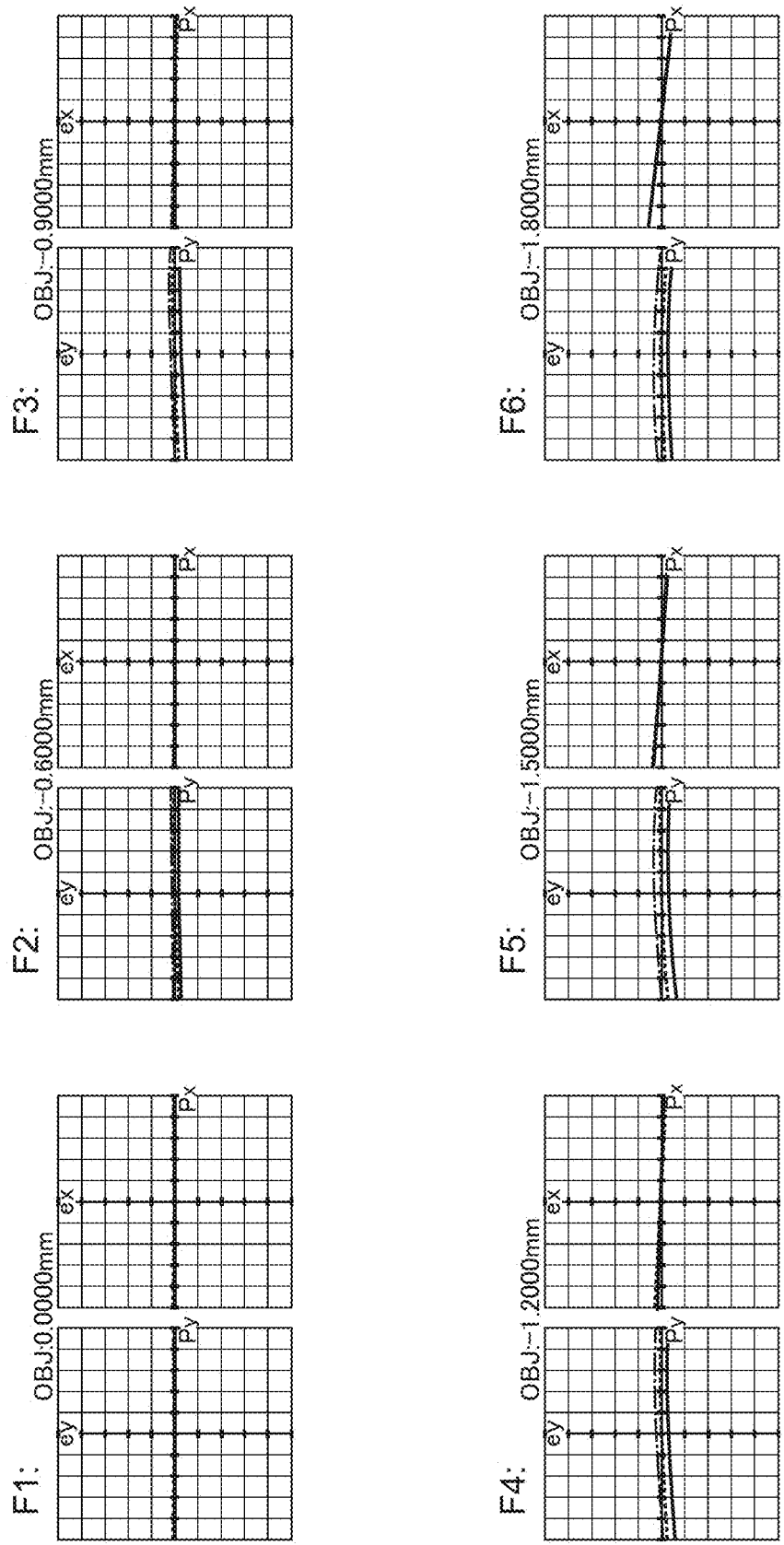

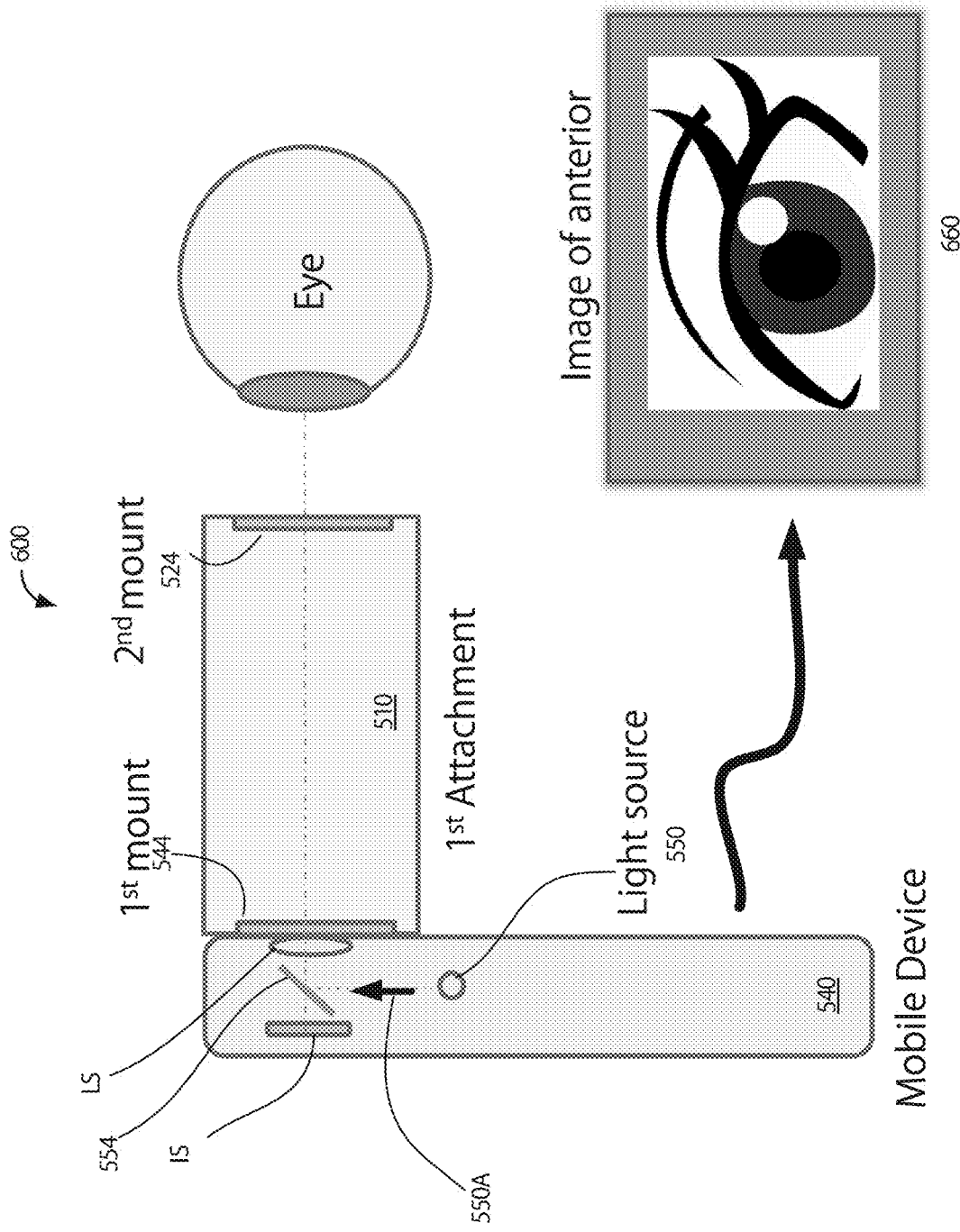

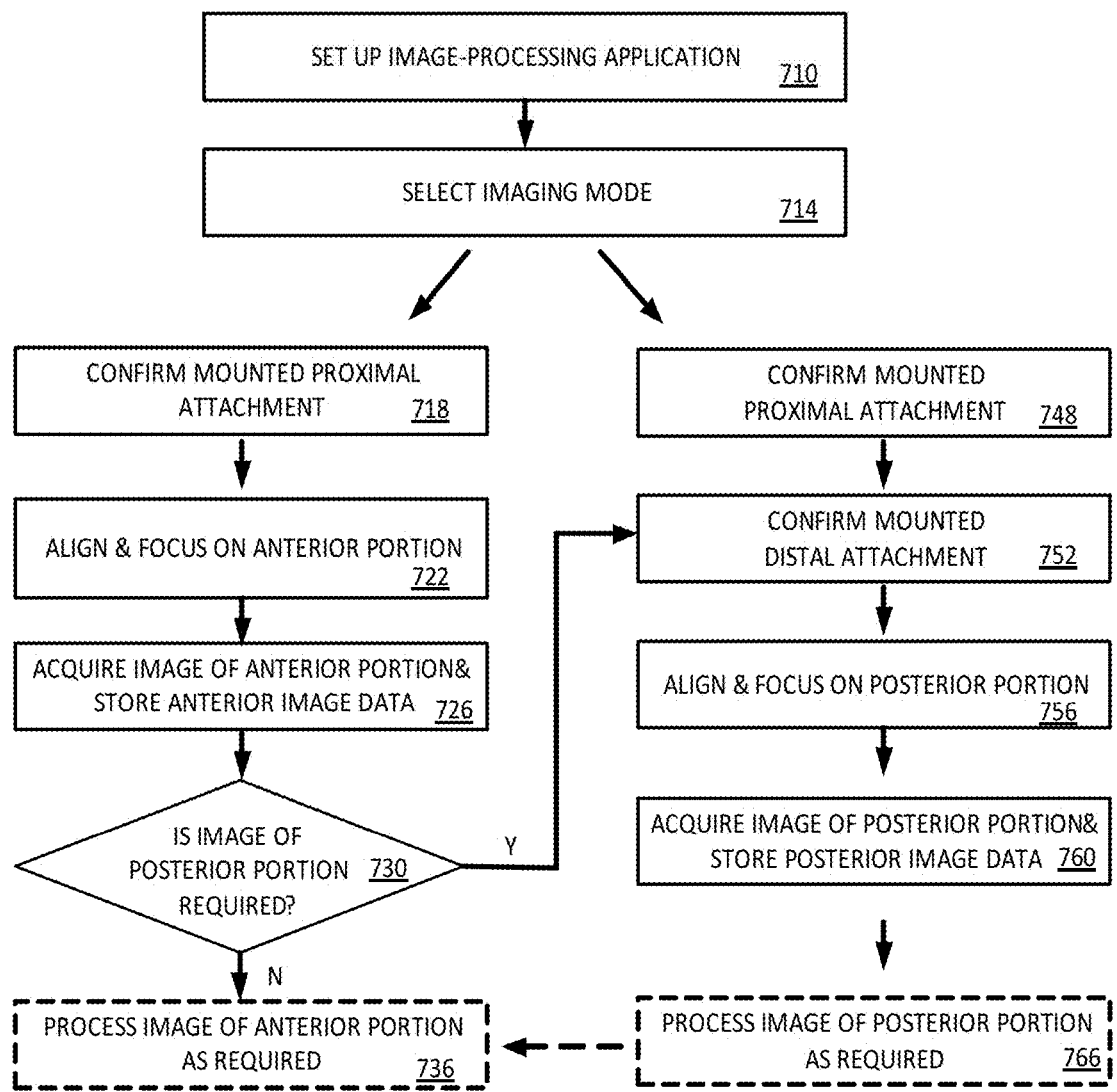

OPTICAL SYSTEM FOR CONVERTIBLE IMAGING OF POSTERIOR AND ANTERIOR PORTIONS OF THE EYE

CROSS-REFERENCE TO RELATED APPLICATIONS

This application is a continuation application of International Application No. PCT/JP2020/023275, filed Jun. 12, 2020, the disclosure of which is incorporated herein by reference in its entirety. Further, this application claims priority from U.S. Patent Application No. 62/861,713, filed Jun. 14, 2019, the disclosure of which is incorporated herein by reference in its entirety.

TECHNICAL FIELD

This invention related generally to ocular diagnostic imaging devices and, more particularly, to a portable handheld smartphone-based (or, generally, a mobile-device-based) optical camera.

BACKGROUND ART

Optical examination of an eye has long history. In some cases, attempts were made to device an optical system that would allow for imaging of both an anterior surface of an eye and a posterior surface of an eye.

The traditional slit-lamp-based arrangement described, for example, in U.S. Pat. No. 2,235,319, was used to visually examine the anterior chamber of the eye. It includes of a low-optical-power microscope that may have either monocular or binocular eyepieces. Then, to view the posterior chamber, or fundus, a so-called "ophthalmic lens" was held in front of the patient's eye-between the slit-lamp-based optical system and the eye- to re-image the retina to the object plane of the slit lamp. (Examples of such ophthalmic lenses are described in U.S. Pat. Nos. 4,222,634, 4,738,521, and 4,627,694, to name just a few.)

It goes without saying that these examples are substantially operationally deficient. At a minimum, the slit-lamp optical system is relatively complicated as it is intended for direct viewing through an eyepiece, so that aberrations have to be well corrected. Further, however, when the ophthalmic lens is added, it also has to be independently well corrected, independently from the slit-lamp-based optical system, in terms of optical performance (otherwise, the imaging of the retinal surface with the originally-used system now complemented with the ophthalmic lens will be, simply put, botched. In practice, however, for the reasons of cost, the ophthalmic lens is not usually corrected for chromatic aberrations—and, in particular, with respect to the lateral color (~ chromatic variation of magnification)—which inevitably leads to chromatic aberrations (manifesting as color fringing) in fundus images. Furthermore, as a person of skill will readily appreciate, such optical arrangement is not landing itself to being easily used in a photography/video tool: although the above-discussed optical combination can be appropriately adapted by adding an optical camera to an eyepiece of the slit lamp, the overall system is then unnecessarily complicated and expensive to manufacture.

WO 2018/043657, the disclosure of which is incorporated by reference herein, describes high-performance telescopic systems that can be used for fundus imaging with a compact camera (such as the one found in cellphones, for example). A given described telescopic system has a focal length and a field-of-view (FOV) that allow such telescope to operate at a magnification that is close to 1× and with a FOV of 80 degrees (full angle) as defined by light distribution entering the eye.

Overall, while digital fundus cameras have been envisioned (some of these on the basis of a cellphone or similar devices such as an iPhone or table; generally, on the basis of a mobile device), such cameras possess substantial operational limitations caused by any of (i) inability to ensure optical conjugation between the optical system of the used mobile device and the vision system (an eye) that is being imaged; (ii) an insufficient field-of-view (FOV) associated with imaging of the chosen surface of the vision system, which results in a need for multiple computational stitching of the multiplicity of acquired images; (iii) severe residual aberrations impairing the resulting images. Furthermore, the envisioned mobile-device-based fundus cameras of the related art have the only, single, and limiting use of providing the fundus imaging—these cameras are not adaptable to do anything else.

While the so-far described systems provide examples of relatively compact and simple designs, certain circumstance still require an even more compact, simpler, and less expensive design that can be easily and reversibly reconfigured, in practice, from a first mode of operation (in which the posterior chamber of an eye is being imaged—for example, a mode of retinal imaging) to a second mode of operation (in which the anterior chamber of the eye is being imaged-for example, the imaging of the iris).

SUMMARY OF INVENTION

An optical imaging system of a first aspect of the technology of the present disclosure, comprising:
a first lens system of an first optical system housed in a body of a mobile telecommunication device, said first lens system having a first optical axis; and
an afocal relay including first and second lenses that possess equal optical properties, the afocal relay configured to have a unity magnification and to provide diffraction-limited imaging within a spectral range from at least 486 nm to at least 656 nm.

A relay optical system of a second aspect of the technology of the present disclosure configured to relay a first plane to a second plane, the relay system comprising:
a first lens having a positive optical power, and
a second lens having a positive optical power, the first and second lenses coaxially and detachably affixed to one another,
wherein, when the first plane corresponds to a first pupil of a subject's eye and the second plane corresponds to a second pupil of an external optical system, the first lens and the second lens form an afocal system configured to form a conjugate relationship between the first plane and the second plane.

A relay optical device of a third aspect of the technology of the present disclosure configured, in combination with an external optical device, to interchangeably image a posterior part of a subject's eye and an anterior part of the subject eye, the relay optical device comprising;
a first tubular member having a first lens with a first positive optical power supported therein and first and second mounts, the first tubular member being removably affixed to the external optical device via the first mount;

a second tubular member having a second lens with a second positive optical power supported therein and a third mount, wherein the second tubular member is coaxially and reversibly mounted to the first tubular member by engaging the third mount with the second mount to optically relay a pupil of the subject's eye to a pupil of an external optical system through the combination of the first and second lenses.

BRIEF DESCRIPTION OF DRAWINGS

FIG. 1C contains spot diagrams corresponding to those locations at the image surface, across the 50 degree field-of-view, which are defined by imaging of the object points at the six given values of the height of the object (F1, F2, . . . , F6, corresponding to those of FIG. 1B);

FIG. 2A schematically illustrates the structural cooperation of a transformed embodiment 200 of the invention (which represents the first half of the embodiment of FIG. 1A) with the wide-angle imaging system of the mobile device. The optical axis of the system corresponds to the z-axis of the local coordinate system;

FIG. 2C contains spot diagrams corresponding to those locations at the surface 114, across the 50 degree field-of-view, which are defined by imaging of the object points at the six given values of the height of the object (F1, F2, . . . , F6, corresponding to those of FIG. 2B);

FIG. 2D schematically illustrates the structural cooperation of the transformed embodiment of FIG. 2A, which represents the first half of the embodiment of FIG. 1A, with the narrow-angle imaging system of the mobile device. The optical axis of the system corresponds to the z-axis of the local coordinate system;

FIG. 2F contains spot diagrams corresponding to those locations at the surface 9 (IMA), across the 25 degree field-of-view, which are defined by imaging of the object points at the six given values of the height of the object (F1, F2, . . . , F6, corresponding to those of FIG. 2E);

FIG. 4B displays six combinations (F1, F2, F3, F4, F5, and F6) of two plots each. These combinations represent ray aberrations on the surface 114 of FIG. 3A across the 50 degree field-of-view for six given values of the height of the object, at chosen wavelengths of the imaging spectrum (R=0.656 microns; G=0.588 microns; B=0.486 microns), both along the y- and x-axes of the local coordinate system;

FIG. 4C contains spot diagrams corresponding to those locations at the surface 114, across the 50 degree field-of-view, which are defined by imaging of the object points at the six given values of the height of the object (F1, F2, . . . , F6, corresponding to those of FIG. 4B);

FIG. 4E displays six combinations (F1, F2, F3, F4, F5, and F6) of two plots each. These combinations represent ray aberrations on the surface 9 (IMA) of FIG. 4D across the approximate 25 degree field-of-view for six given values of the height of the object, at chosen wavelengths of the imaging spectrum (R=0.656 microns; G=0.588 microns; B=0.486 microns), both along the y- and x-axes of the local coordinate system;

FIG. 6 is a schematic of the transformed imaging system configured to image an anterior ophthalmic surface;

FIG. 7 is a simplified flow-chart illustrating a sequence of steps associated with the process of imaging a selected portion of an eye.

DESCRIPTION OF EMBODIMENTS

Figure 1A:
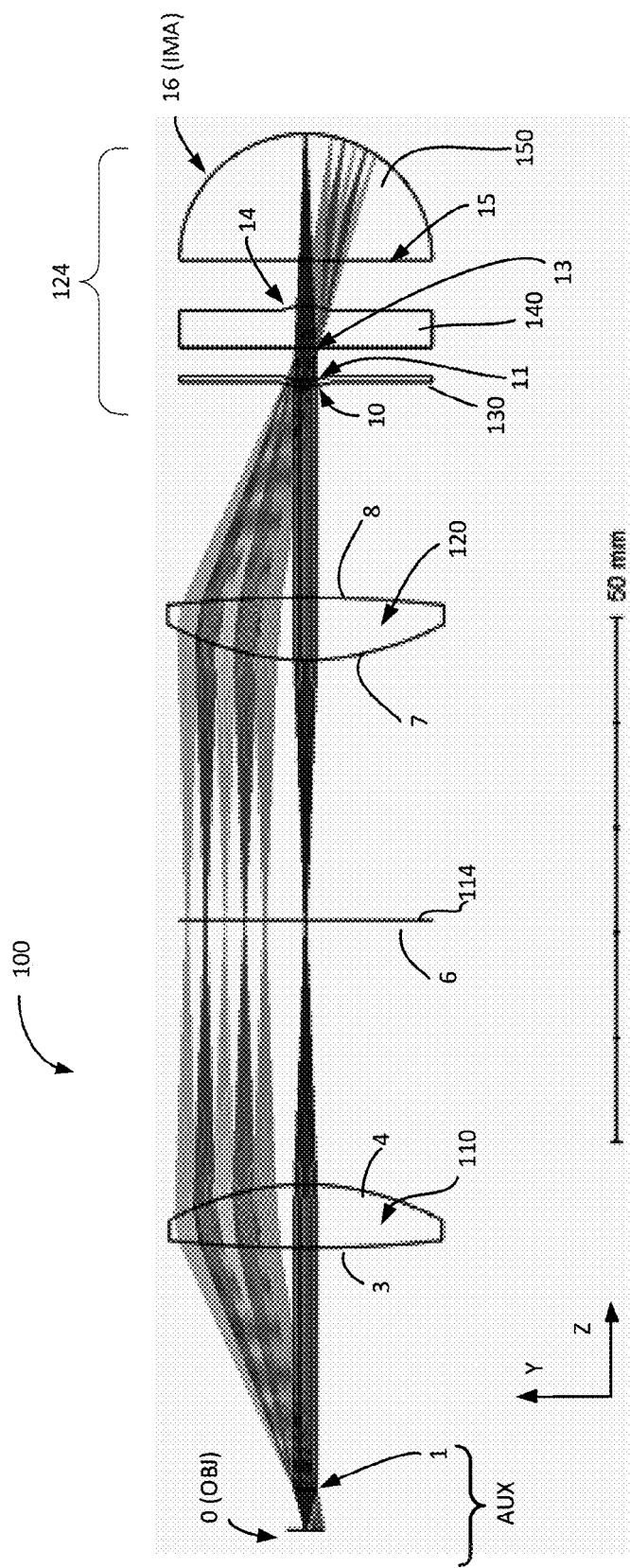
FIG. 1A schematically illustrates the structural cooperation of an embodiment of the posterior-surface-of-the-eye-imaging optical system of the invention (~50 degree field diameter), utilizing two identical lens elements, with the imaging system of the mobile device and the eye being imaged. The optical axis of the system corresponds to the z-axis of the local coordinate system.

Embodiments of the present invention address optical systems and methodologies of operating such optical systems that solve a multiplicity of shortcomings of art related to ophthalmological imaging. In particular:

The problem of inability of prior art to provide a structurally-transformable optical system (configured as a fundus optical camera), which is devised to be re-configured from operation in the mode of imaging a posterior surface of an eye (for example, the retinal surface) to the mode of imaging an anterior surface of the eye (for example, the surfaces of the cornea, iris, and/or eye-lens) and vice versa is solved by configuring the fundus camera to include no more than two optical lenses that are optically-matched, identical with respect to one another in both geometrical and optical characteristics so as i) to ensure an afocal optical relay possessing with a unity (1×) magnification and, in operation, ii) to remove one of such matched lenses to achieve the required transformation of the system to an optical magnifier. The reverse transformation is easily performed by adding an optically-matching lens to another such lens. Notably, embodiments of the present invention ensure such structural transformation and while maintaining a wide FOV sufficient for cooperation of the optical system with an imaging system of a mobile device (such as a cellular phone, for example)—in particular, with an imaging system of the mobile device that includes multiple objectives.

As used herein, the terms "posterior portion" or "posterior surface" of the eye or similar terms refer to a segment of the eyeball located approximately within the back two-thirds of the eye that includes the anterior hyaloid membrane and all of the optical structures behind it: the vitreous humor, retina, choroid, and optic nerve. Accordingly, the terms "anterior portion" or "anterior surface" of the eye or similar terms refer to the front third of the eye that includes the structures in front of the vitreous humour: the cornea, iris, ciliary body, and lens.

As used herein, both the terms "lens" and "lens element" define an optical device operating in transmission and converging or diverging light passing through the device by means of optical refraction. Such optical device has two monotonically-curved surfaces, front and rear, each of which has a corresponding radius of curvature and both of which are transverse to the optical axis of the device. In this context, however, the term "lens element" represents and denotes a simple lens or lenslet the refractive index of the material of which remains substantially constant between the front and rear surfaces. The term "lens", on the other hand, refers to either the lens element or to a compound lens that is a collection of simple constituent lenses of generally different shapes and made of materials of generally different refractive indices, arranged one after the other with a common axis as long as the facing-each-other surfaces of such simple constituent lenses are in physical contact with each other at every point of such surfaces. For example, an optical doublet and an optical triplet may be characterized as lenses (containing two or three lens elements, respectively) but not lens elements, while an optical meniscus can be characterized as either a lens or a lens element.

In a particular embodiment, embodiments of the convertible fundus camera of the invention include only two matched optical lenses. In one specific implementation, each of the only two optically-matched lenses contains a single, stand-alone lens element. In such specific implementation, when configured for imaging of the posterior ophthalmic surface, the telescopic system possesses the FOV of about 50 degrees, and when reconfigured to the loupe for an anterior eye-camera (by removing one of the optically-matched lenses)—a FOV of about 12.5 mm in diameter (full field), which dimensionally corresponds to the size of the cornea. In another specific implementation, each of the only two optically-matched lenses represents an optical doublet.

Just like in the case of WO 2018/043657, it is preferred that the reversibly-restructurable implementation of the proposed optical system be complemented and operate with an optical system with which a typical cellphone is equipped (or another compact optical camera that has an aperture with a dimension that is close to that of an un-dilated eye pupil, of about 2 mm in diameter). In case of a typical optical camera of a cell-phone, the FOV of such optical camera is 50 degrees (full field) along the axis corresponding to the short dimension of the rectangular display format of the camera. Accordingly, there is no practical reason for an optical relay, with which the camera of a cell-phone is complemented to image a surface of the eye, to possess the FOV in access of 50 degrees. In an embodiment of the invention, the spatially-congruent surfaces of the two optically-matched lenses are disposed to face each other.

A skilled artisan will readily appreciate from the following disclosure that even aside from the clear operational advantages of the structural simplicity and resulting extremely-low cost, the implementation of the idea of the present invention drastically improves the operation of any embodiment discussed in WO 2018/043657. The immediate reasons for such advantageous improvement stem from the fact that the system(s) of WO 2018/043657 operate at a magnification that may be close to 1× but are not equal to 1×, while the optical magnification of the proposed optical structure(s) necessarily equals to one, thereby by its very nature avoiding (being devoid of, not possessing, not being characterized with) the lateral chromatic aberrations (that is the variation of magnification as a function of wavelength), come, and distortion. At least the same characteristics clearly differentiate an embodiment of an afocal relay of the invention, configured to operate in a dual mode as a result of removing one of the two optically-matching lens elements, from the systems of US 2016/0296112, US 2018/0153399, and U.S. Pat. No. 9,706,918.

The same exact 1×-magnification symmetry of the proposed embodiments minimizes the manufacturing costs by allowing the use of the identical, matched lenses (each of the substantially 40 diopters of optical power) to achieve the 50-degree FOV with an about 20 mm eye-relief.

Some notes are in order (these relate to and are applicable to each of the embodiments discussed below):

The examples of prescription(s) of implementation(s) of an optical system of the imaging system according to the idea of the invention and the subsystems of such implementations, performed with the optical design program Zemax, are summarized in multiple Tables (below) and are discussed in reference to corresponding Figures. Here, optical elements and surfaces are numbered in a "backward" fashion, starting with an element labeled as "object"/"OBJ". The substantially collimated beams of lights from the object points are delivered by the auxiliary lens (that is part of the mobile device used in conjunction with embodiments of the imaging camera) to the first lens of the embodiment (labeled as 110, 310 in the Figure(s)), then through the second lens of the embodiment (labeled as 120, 320 in the Figures), and so on and towards the user's eye (represented by the Navarro model of the eye, as known in the art), which makes it easier to define the NA and other optical parameters in the space of the eye during the process of optical design. Accordingly, a dimeter or radius of the image denotes the dimension of an "object" imaged in light delivered through the embodiment of the objective onto the retina of the eye (i.e., onto the "image surface").

Positive value of a radius of curvature of a curved surface indicates the center of the curvature that is to the right of the curved surface, while a negative radius value indicates the center of the curvature that is to the left of the curved surface; dimensions are provided in millimeters; thickness is defined as an axial distance to the next surface; and an image diameter shown is a paraxial value and not a ray-traced value. As is conventionally understood, a value of a radius of curvature of a given surface a value of curvature of such surface are reciprocal to one another.

Single- and double-digit numeral designations of optical surfaces used for ZEMAX-based designs used in each of the Examples presented below are specific to a given design and do not carry over from design to design. In other words, surfaces labelled, for example, as "3" or "15" in different Figures pertaining to different designs are not necessarily the same- and are likely different from one another-surfaces. The same is the case for designations of plots or combination of plots referred to as F1 through F6 in various Figures: these designations are Figure-specific.

At the same time, the three-digit numeral designations of optical components or elements remain the same throughout different designs and refer to the same optical components or elements. For example, the designation "110" of the lens element in one of the designs refers to the same lens in a different design.

A detailed description of the Navarro eye model in Zemax is presented at customers.zemax.com/os/resources/learn/knowledgebase/zemax-models-of-the-human-eye, and is incorporated by reference herein. (Based on that description, the sequential model, referred to as Eye_Retinal Image, was used in this design.)

In one embodiment, described in reference to FIGS. 1A, 1B, 1C, 2A through 2F, the constituent lenses are configured as simple lenses or individual lens elements, while in a related embodiment (described in reference to FIGS. 3A through 3C and 4A through 4F), the constituent lenses are configured as optical doublets. In each of the full-length imaging systems of each of the first and second embodiments (configured for imaging of the posterior surface of the eye), the FOV of the system at the surface of the intermediate image (between the constituent lenses) is judiciously designed to be substantially equal to 25 mm in diameter, which is what is required for imaging the front portion of the eye. Accordingly, each of the full-length systems of the first and second embodiments can be and is easily converted to a half-length imaging system (without disturbing the mechanical cooperation between the first lens of the system and the mobile device) by removing the second of the constituent lenses, to image the anterior portion of the eye.

Example 1: A Full-Length System Configured for Imaging of a Posterior Surface of the Eye In reference to FIG. 1A and the data of Table 1, the embodiment 100 of the rotationally-symmetric dioptric afocal relay, telescope (as shown in the yz-cross-section) is used to optically relay the light from the chosen object to the retina of the eye. FIG. 1A and Table 1 represent the ZEMAX data that describe the surfaces of the optical train of the elements of the embodiment 100 and surfaces corresponding to auxiliary surfaces of the object, intermediate optical objects, and those of the eye.

The person of skill in the art will readily appreciate that, for the purpose of simplification of the optical system design, the raytracing was carried out in a reversed direction—from the surface of the optical detector to the ophthalmological surface of interest. As a result, in the design the object (surface "0", also denoted as OBJ, on left of above diagram) represents the surface of the imaging sensor (interchangeably denoted herein as IS, throughout the Figures and the description) of a mobile device (for example, a cellphone camera sensor) with a 3.6 mm diameter (which diameter is equal to the diagonal of the rectangular sensor format), in combination with which the embodiment 100 may be used for imaging an ocular surface of interest. The image surface is the retinal surface 16, also denoted as IMA.

The stop, or pupil, surface 1 (also denoted as STOP), represents the wide-angle lens of the cellphone camera, which is in Zemax described as a zero-aberration paraxial lens, disposed at a distance of about 3.9 mm from the imaging sensor of the camera denoted as surface) or OBJ. Generally, a lens of the mobile device such as a cellphone (whether a wide-angle lens or a narrow-angle lens) is interchangeably denoted herein as LS, throughout the Figures and the description. (The separation between the surfaces 0 and 1 is substantially equal to the focal length of the typical wide-angle cellphone camera lens, which in these calculations is assumed to be a perfect lens.) Accordingly, the combination of optical elements 0 and 1, denoted as AUX in FIG. 1A, represents the imaging system of the auxiliary, external to the embodiment 100 device (such as a mobile device, cellphone in particular). The intermediate image is formed in surface 6.

The human eye 124 is modelled according to the Navarro eye model (optical elements 130, 140, and 150) and is represented by surfaces 10-15, with the image formed at retina (surface 16). The corneal surfaces are denoted 10 and 11, the front surface of the eye-lens is 13 and the back surface of the eye-lens is surface 14. The retina of the eye is represented, in this example, by a hemispherical surface of a radius with absolute value of 12 mm. Various aberrations are evaluated on that spherical surface 16 (which is the reason why the raytracing is performed from the camera sensor, surface 1, to the eye).

(As shown in the Table 1 below, a skilled optical designer will understand that at least surfaces 2, 5, 9, 12 were used as dummy surfaces simplifying the ZEMAX model set-up. Surface 2 is substantially in contact with surface 1; surface 5 is substantially in contact with surface 4; surface 9 precedes the component 130 of the Navarro eye-model; while surface 12 represents the eye-pupil and is in between the rear corneal surface 11 and the front surface 13 of the lens of the eye.)

Notably, all optical surfaces of the embodiment 100 are "standard" surfaces (in terminology used in Zemax), which are conic surfaces (the description of which contains no aspheric terms other than a specified conic constant). In the case of spherical surfaces, the conic constant is zero (the value is left blank/empty in Table 1).

When mechanically-cooperated with the lens of the mobile device at a separation of about 23 mm from the lens of the mobile device, the telescope 100 of the invention is configured to straightforward imaging of the posterior surface of the eye (for example, fundus).

It is understood, therefore, that the embodiment 100 provides a relay optical system including first and second positive lenses. The first lens has a biconvex shape and first and second surfaces that have, respectively, first and second surface curvatures (the first surface curvature being larger than the second surface curvature). The second lens is also dimensioned in a biconvex fashion and has third and fourth surfaces (that have, respectively, third and fourth surface curvatures, the third surface curvature being larger than the fourth surface curvature). The first and second lenses are mutually oriented to have the first and third surfaces face one another. The first and second lenses may be formatted to be substantially identical to one another to form a symmetrical optical system characterized by unit magnification. In general, each of the first and second lenses may be dimensioned to satisfy the condition of $0.2 < |Q| < 0.8$, where $|Q| = (R_b + R_a)/(R_b - R_a)$. Here, $R_a$ represents the larger radius of curvature between the radii of curvature of the two surfaces of a given lens, and $R_b$ represents the smaller radius of curvature between the radii of curvature of the two surfaces of such given lens.

(Notably, the corrective effect may be reduced by the fact that irradiance of light backscattered by the retina is several times stronger in the red portion of the visible spectrum than in the blue portion). In a related implementation of imaging the retina, one could take separate exposures in either red or green portions of the visible spectrum, refocusing in between exposures, or red, green and blue exposures for a better white balance. A person of skill will readily appreciate that some value of the lateral color may be present in the plots of FIG. 1B: such lateral color aberration is introduced by the eye itself.

FIG. 1C characterizes the imaging performance of the embodiment 100 and shows the spot diagrams in the image surface for the same object fields numbered F1, F2, . . . , F6. The Airy radius is 5.962 µm. The rms radii of the spot diagrams at the image surface, corresponding to imaging of the object points representing these object fields are 13.616 µm, 15.261 µm, 16.802 µm, 18.446 µm, 20.322 µm, and 23.334 µm, respectively.

TABLE 1

SURFACE DATA SUMMARY for Embodiment of FIG. 1A:

| Surface | Type | Radius | Thickness | Glass Nd | Vd | Clear Diameter | Conic Constant |
|---|---|---|---|---|---|---|---|
| 0 (OBJ) | STANDARD | Infinity | 3.9 | | | 3.6 | |
| 1 (STOP) | PARAXIAL | Infinity | 0 | | | 2.0 | |
| 2 | STANDARD | Infinity | 23 | | | 2.1 | |
| 3 | STANDARD | 120.7157 | 6 | 1.788 | 47.369 | 24.96086 | |
| 4 | STANDARD | −23.8311 | 0 | | | 25.89657 | −1.510853 |
| 5 | STANDARD | Infinity | 25.18358 | | | 25.70774 | |
| 6 | STANDARD | Infinity | 24.72201 | | | 24.16831 | |
| 7 | STANDARD | 23.8311 | 6 | 1.788 | 47.369 | 26.25385 | −1.510853 |
| 8 | STANDARD | −120.7157 | 17.97694 | | | 25.36686 | |
| 9 | STANDARD | Infinity | 2.09 | | | 7.428863 | |
| 10 | STANDARD | 7.72 | 0.55 | 1.375 | 61.513 | 5.044004 | −0.26 |
| 11 | STANDARD | 6.5 | 3.05 | 1.337 | 52.659 | 4.963477 | |
| 12 | STANDARD | Infinity | 0.0001 | 1.337 | 52.659 | 2.420566 | |
| 13 | STANDARD | 10.2 | 4 | 1.420 | 51.226 | 2.467866 | |
| 14 | STANDARD | −5 | 4.92 | 1.336 | 53.382 | 4.690983 | −1 |
| 15 | STANDARD | Infinity | 12 | 1.336 | 53.342 | 7.64985 | |
| 16 (IMA) | STANDARD | −12 | | 1.336 | 53.347 | 24.0 | |

As seen from FIG. 1A and Table 1, the design 100 employs one conic aspheric surface for each of the constituent ophthalmic lenses 110, 120.

Figure 1B:
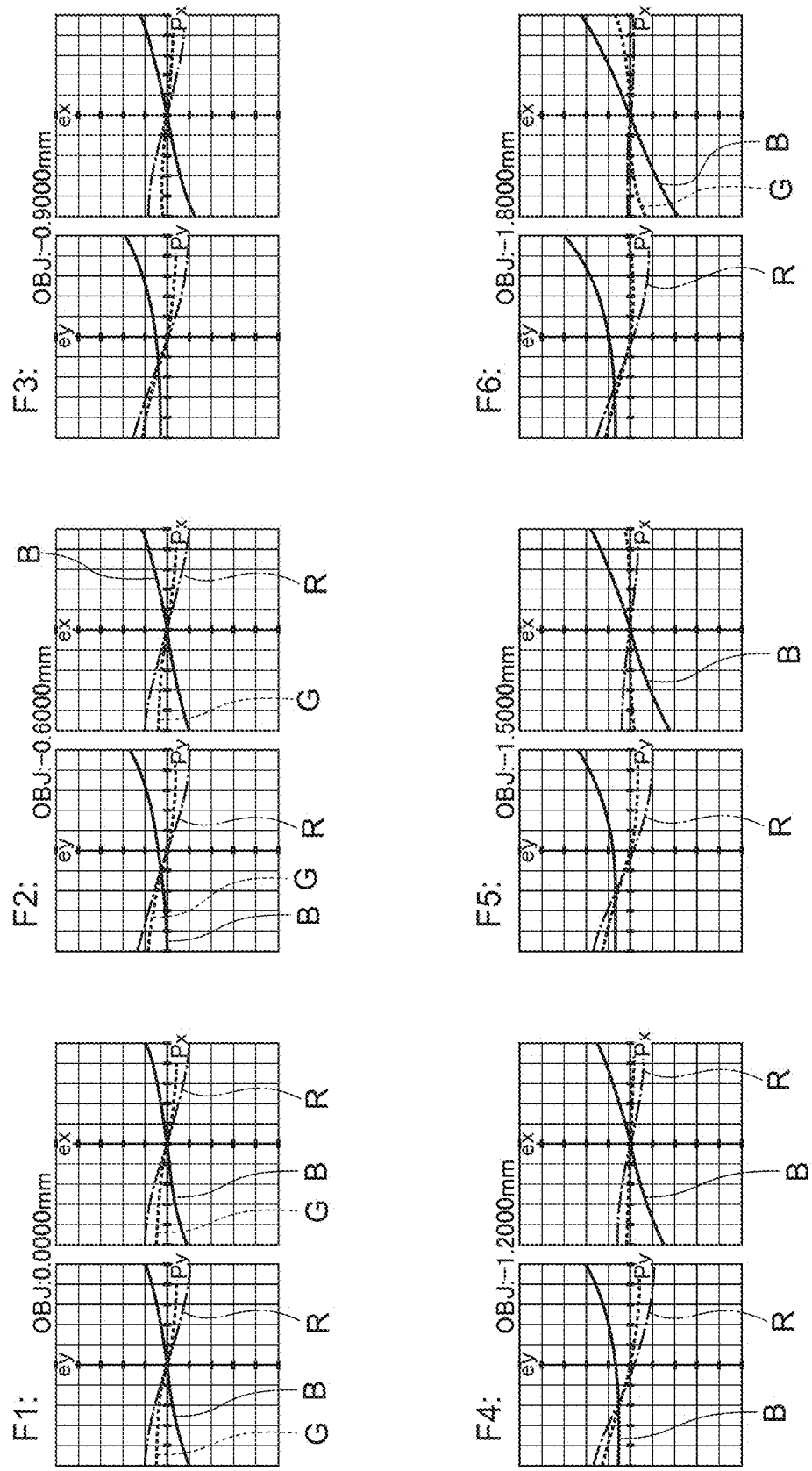
FIG. 1B displays six combinations (F1, F2, F3, F4, F5, and F6) of two plots each. These combinations represent ray aberrations on the retinal surface across the 50 degree field-of-view for six given values of the height of the object, at chosen wavelengths of the imaging spectrum (R=0.656 microns; G=0.588 microns; B=0.486 microns), both along the y- and x-axes of the local coordinate system.

FIG. 1B displays the transverse ray fan plots at the image surface (denoted as IMA in FIG. 1A), representing primarily axial color aberrations (that is, a chromatic variation of position of a focal point). Here, the maximum scale for each of the plots is +/−100 microns. The ray fan plots are presented for different heights of the object (that is, for different object fields numbered F1, F2, . . . , F6, where the absolute value of the height of the object point in field F1 is chosen to be zero, in F2: 0.6 mm, and in the largest field F6: 1.8 mm). While a person of skill readily appreciates that the residual axial color aberrations can be corrected with the use of appropriately-designed optical doublets in place of lens elements 110, 120, the use of optical doublet increases the costs of the overall system. Therefore, if the goal is to maintain the design including only single lens elements, it is possible to at least partially correct for axial color aberrations by processing the resulting images of the retina of the eye with image-processing software, either embedded/pre-programmed in the processor of the mobile device or during post-processing.

Example 2: Transformation of the Full-Length System 100 to Image a Chosen Anterior Surface of the Eye The operational advantage of the embodiment 100 of the invention manifests in the fact that that embodiment is easily transformable, changeable into a simplified version that is immediately adopted, in conjunction with the imaging system of the same auxiliary device (such as the cell phone, for example) for imaging a different ophthalmic surface. The transformation of the embodiment 100 is rather trivial, and stems from removing a lens that is distal to the auxiliary device (in reference to FIG. 1A-removing the lens 120). A skilled person will appreciated that, as a result of such transformation, the substantially-symmetric telescopic system 100 is turned into what may be classified as an optical magnifier.

To this end, FIG. 2A schematically illustrates the structural cooperation of a transformed embodiment 200 of the invention (which represents the first half of the embodiment of FIG. 1A) with the wide-angle imaging system of the mobile device. The optical axis of the system corresponds to the z-axis of the local coordinate system. The prescription for the optical train of the imaging system 200 of FIG. 2A and Table 2A represents and corresponds to the first half of the system 100 (comprising the optical surfaces from the object OBJ, representing an imaging sensor of an imaging camera, to and including that representing the intermediate image surface 6, 114 of FIG. 1A). Such half-system if formed when the second lens 120 of the system 110 is removed from the embodiment 100. As a result of such transformation, the surface 6 of FIG. 1A becomes the ophthalmological (eye) surface 210 that is located in front of the retinal surface 16 and that is now subject to imaging with the embodiment 200 through the objective lens (represented by 1) of the imaging camera of a mobile device onto the surface of the imaging sensor (represented by O, OBJ) of the mobile device. The total axial length is about 58.06 mm. In one example, the ophthalmological surface 210 is a surface substantially in contact with the anterior surface of the cornea, and has a diameter of about 24 mm. The FOV of the embodiment 200 is about 50 degrees and this is large enough to cover the whole front of the eye.

Figure 2B:
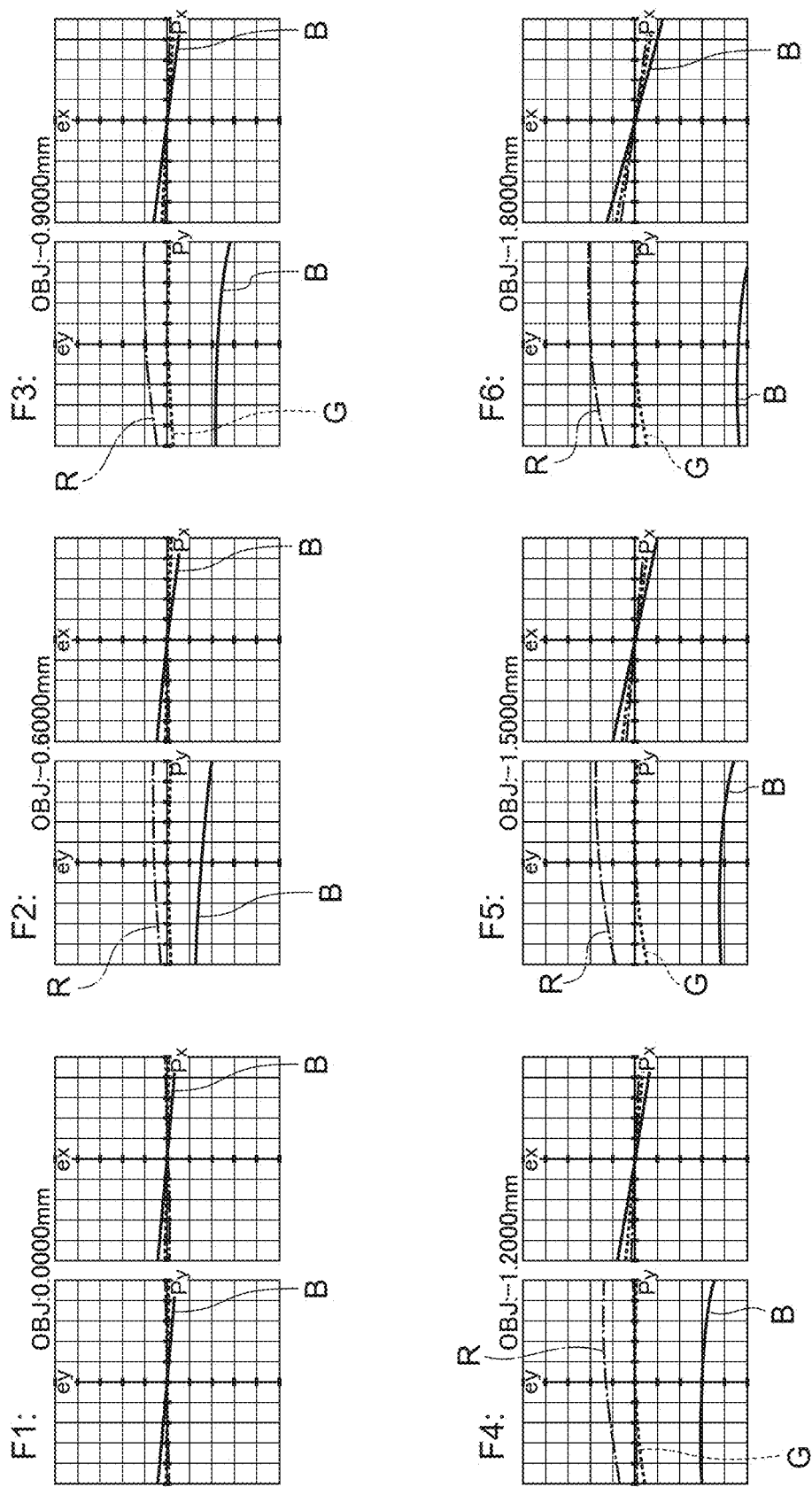
FIG. 2B displays six combinations (F1, F2, F3, F4, F5, and F6) of two plots each. These combinations represent ray aberrations on the surface 114 of FIG. 1A across the 50 degree field-of-view for six given values of the height of the object, at chosen wavelengths of the imaging spectrum (R=0.656 microns; G=0.588 microns; B=0.486 microns), both along the y- and x-axes of the local coordinate system.

FIG. 2B displays six combinations (F1, F2, F3, F4, F5, and F6) of two plots each. These combinations represent ray aberrations on the surface 6 of FIG. 2A (corresponding to surface 6, 114 of FIG. 1A) across the 50 degree field-of-view for six given values of the height of the object, at chosen wavelengths of the imaging spectrum (R=0.656 microns; G=0.588 microns; B=0.486 microns), both along the y- and x-axes of the local coordinate system. FIG. 2C contains spot diagrams corresponding to those locations at the surface 114, across the 50 degree field-of-view, which are defined by imaging of the object points at the six given values of the height of the object (F1, F2, . . . , F6, corresponding to those of FIG. 2B);

It is appreciated, therefore, that as a result of a simple transformation from the embodiment 100 of the fundus camera to the embodiment 200 of the optical magnifier, an additional degree of operational freedom has been gained-specifically, to image yet another ophthalmological surface (of the eye) in addition to the retinal surface with the same imaging system of the same auxiliary (external to the embodiments of the invention, for example, mobile) device as that used with the embodiment 200.

Example 3: Transformation of the Full-Length System 100 to Image a Second Anterior Surface of the Eye Notably, the embodiment 100 of the invention transformed as a result of removing the lens 120 can also be used in a situation when the imaging system of the auxiliary device is a dual-imaging system—for example, when in addition to the wide-angle lens the mobile device such as the cell-phone is equipped with a second, narrow-angle camera lens. In this case- and assuming that the connector between the embodiment of the optical system of the invention and the mobile device is equipped with some sort of a translational stage configured to relatively reposition the optical system of the embodiment of the invention from the first camera lens of the mobile device to the second camera lens of the mobile device—the transformed embodiment 200 can be employed for imaging of yet another anterior surface of the eye, the angular extent of which approximately corresponds to the FOV of the second camera lens of the auxiliary device.

TABLE 2A

SURFACE DATA SUMMARY: Cooperation of a Wide-Angle Lens with Embodiment 200:

| Surface | Type | Radius | Thickness | Nd | Vd | Clear Diameter | Conic Constant |
|---|---|---|---|---|---|---|---|
| 0 (OBJ) | STANDARD | Infinity | 3.9 | | | | |
| 1 (STOP) | PARAXIAL | Infinity | 0 | | | 2 | |
| 2 | STANDARD | Infinity | 23 | | | 2.1 | |
| 3 | STANDARD | 120.7157 | 6 | 1.788 | 47.369 | 24.96086 | |
| 4 | STANDARD | −23.8311 | 0 | | | 25.89667 | −1.510853 |
| 5 | STANDARD | Infinity | 25.16356 | | | 25.70774 | |
| 6 (IMAGE) | STANDARD | Infinity | | | | 24 | |

TABLE 2B

SURFACE DATA SUMMARY: Cooperation of a Narrow-Angle Lens with Embodiment 200:

| Surface | Type | Radius | Thickness | Nd | Vd | Clear Diameter | Conic Constant |
|---|---|---|---|---|---|---|---|
| 0, OBJ | STANDARD | Infinity | 8 | | | 3.6 | |
| 1′, STOP | PARAXIAL | Infinity | 0 | | | 2 | |
| 2 | STANDARD | Infinity | 23 | | | 2.1 | |
| 3 | STANDARD | 120.7157 | 6 | 1.788 | 47.36 | 24.9606 | |
| 4 | STANDARD | −23.8311 | 0 | | | 25.89667 | −1.580853 |
| 5 | STANDARD | Infinity | 22 | | | | |
| 6 | STANDARD | 7.72 | 0.55 | 1.375 | 61.513 | 12.19496 | −0.26 |
| 7 | STANDARD | 6.5 | 3.05 | 1.337 | 52.659 | 11.56292 | |
| 8 | STANDARD | Infinity | 0.0001 | 1.337 | 52.659 | 12.56018 | |
| 9, IMAGE | STANDARD | Infinity | | 1.337 | 52.659 | 12.0 | |

Figure 2E:
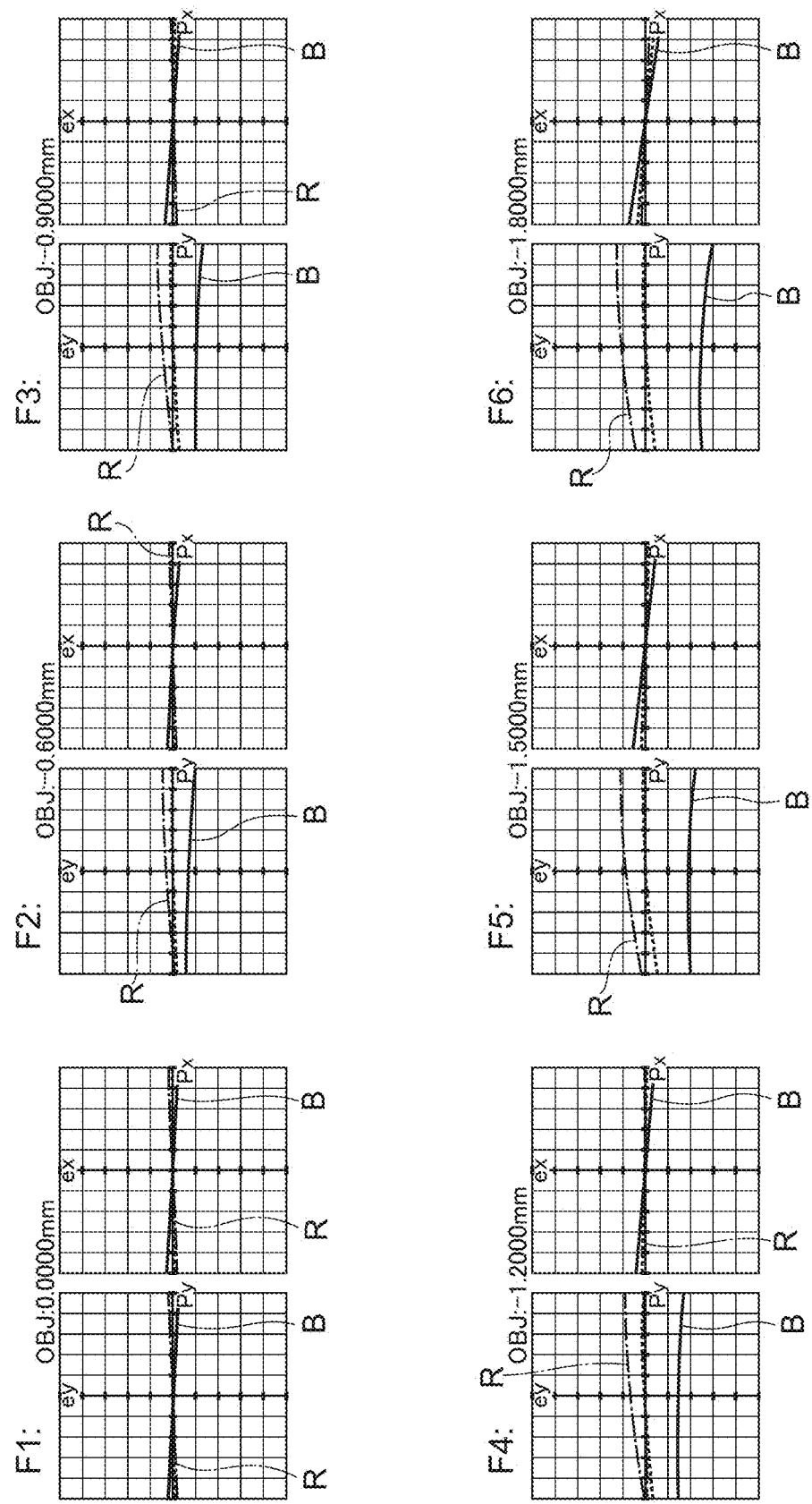
FIG. 2E displays six combinations (F1, F2, F3, F4, F5, and F6) of two plots each. These combinations represent ray aberrations on the surface 9 (IMA) of FIG. 2D across the approximate 25 degree field-of-view for six given values of the height of the object, at chosen wavelengths of the imaging spectrum (R=0.656 microns; G=0.588 microns; B=0.486 microns), both along the y- and x-axes of the local coordinate system.

An example of such use is represented by FIGS. 2D, 2E, 2F and Table 2B. In this narrow-angle case (FOV ~ 25 degrees), the combination of the narrow-angle camera lens of the mobile device and the embodiment 250 is configured to image another anterior surface of the eye (the one different from the corneal surface)—for example, the surface of the eye's iris that is immersed in aqueous humor.

Here, FIG. 2D schematically illustrates the structural cooperation of the transformed embodiment 200 of FIG. 2A (which represents the first half of the embodiment of FIG. 1A) with the narrow-angle imaging system of the auxiliary mobile device. The optical axis of the system corresponds to the z-axis of the local coordinate system. In reference to FIG. 2D and Table 2A, the stop, or pupil, surface 1' (also denoted as STOP), represents the narrow-angle lens of the cellphone camera, which is in Zemax described as a zero-aberration paraxial lens, disposed at a distance of about 8.0 mm from the camera's imaging sensor that is denoted as surface 0 or OBJ. (The separation between the surfaces 0 and 1' is substantially equal to the focal length of the typical narrow-angle cellphone camera lens, which in these calculations is assumed to be a perfect lens.) Accordingly, the combination of optical elements 0 and 1', denoted as AUX' in FIG. 2D, represents the imaging system of the device that is auxiliary, external to the embodiment 200 (such as a mobile device, cellphone in particular). The total axial length is about 62.6 mm. A skilled artisan will appreciate that some of the surfaces described in Table 2B are dummy surfaces used for the purposes of efficient set-up of the ZEMAX design model, as commonly used in the art. The diameter of the image field (at surface IMA) is 11 mm, which is large enough to cover most of the fully-dilated iris.

FIG. 2E complements the description of the use of the transformed embodiment of the invention with the narrow-angle imaging lens of the mobile device by displaying six combinations (F1, F2, F3, F4, F5, and F6) of two plots each. Maximum scale is +/−200 microns. These combinations represent ray aberrations on the surface 9 (IMA) of FIG. 2D across the approximate 25 degree field-of-view for six given values of the height of the object, at chosen wavelengths of the imaging spectrum (R=0.656 microns; G=0.588 microns; B=0.486 microns), both along the y- and x-axes of the local coordinate system.

Finally, FIG. 2F contains spot diagrams corresponding to those locations at the surface 9 (IMA), across the 25 degree field-of-view, which are defined by imaging of the object points at the six given values of the height of the object (F1, F2, . . . , F6, corresponding to those of FIG. 2E).

Figure 3A:
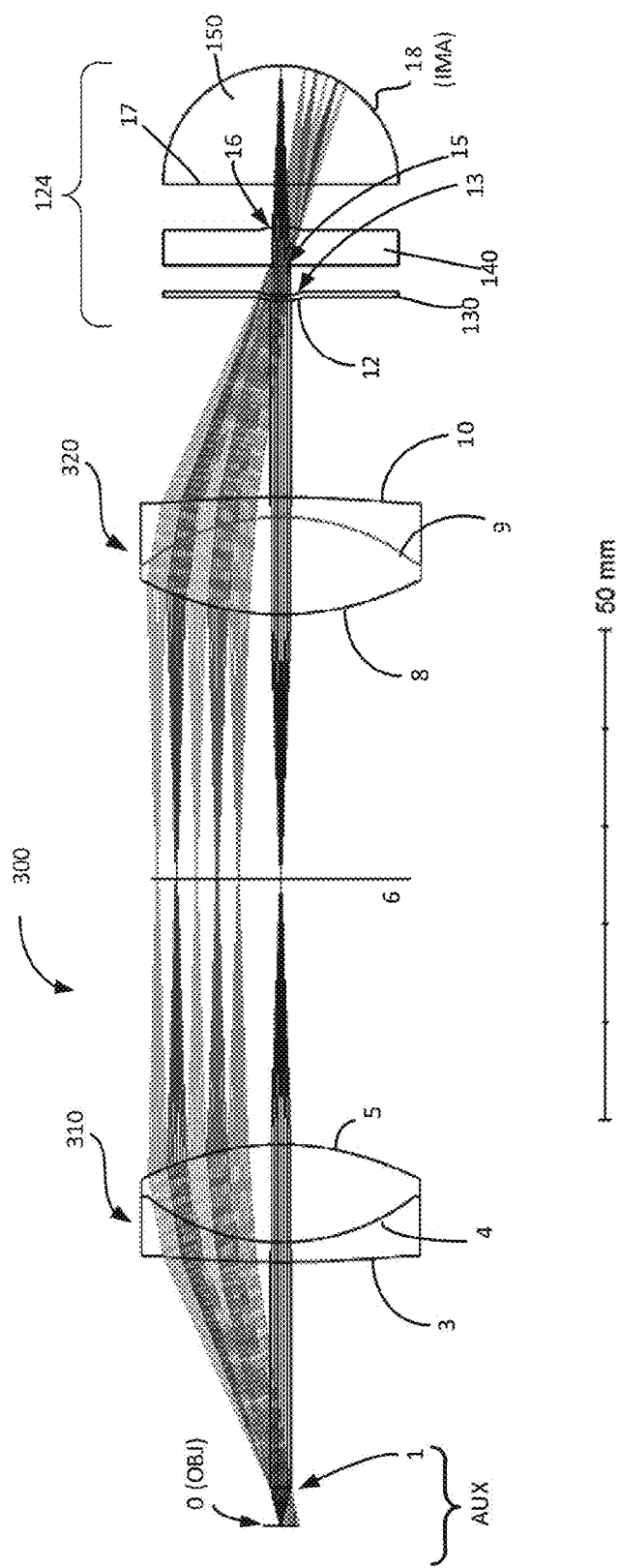
FIG. 3A schematically illustrates the structural cooperation of an alternative embodiment 300 of the posterior-surface-of-the-eye-imaging optical system of the invention (~ 50 degree field diameter), utilizing two identical optical doublets, with the imaging system of the mobile device and the eye being imaged. The optical axis of the system corresponds to the z-axis of the local coordinate system.

Example 4: A Related Full-Length System Configured for Imaging of a Posterior Surface of the Eye In reference to FIG. 3A and the data of Table 3, the embodiment 300 of the rotationally-symmetric dioptric afocal relay, telescope (as shown in the yz-cross-section) is used to optically relay the light from the chosen object to the retina of the eye. FIG. 3A and Table 3 represent the ZEMAX data that describe the surfaces of the optical train of the elements of the embodiment 300 and surfaces corresponding to auxiliary surfaces of the object, intermediate optical objects, and those of the eye. Here, constituent lenses 310, 320 are configured as two identical cemented achromatic doublets (and not single lens elements, in contradistinction with the embodiment 100).

The person of skill in the art will readily appreciate that, for the purpose of simplification of the optical system design, the raytracing was carried out in a reversed direction—from the surface of the optical detector to the ophthalmological surface of interest. As a result, in the design the object (surface "0", also denoted as OBJ, on left of above diagram) represents the surface of the of imaging sensor of a mobile device (for example, cellphone camera sensor) with a 3.6 mm diameter (which diameter is equal to the diagonal of the rectangular sensor format), in combination with which the embodiment 300 may be used for imaging an ocular surface of interest. The image surface is the retinal surface 18, also denoted as IMA.

The stop, or pupil, surface 1 (also denoted as STOP), represents the wide-angle lens of the cellphone camera, which is in Zemax described as a zero-aberration paraxial lens, disposed at a distance of about 3.9 mm from the imaging sensor of the camera denoted as surface) or OBJ. (The separation between the surfaces 0 and 1 is substantially equal to the focal length of the typical wide-angle cellphone camera lens, which in these calculations is assumed to be a perfect lens.) Accordingly, the combination of optical elements 0 and 1, denoted as AUX in FIG. 3A, represents the imaging system of the auxiliary, external to the embodiment 300 device (such as a mobile device, cellphone in particular).

The intermediate image is formed in surface 6.

The human eye 124 is modelled according to the Navarro eye model (optical elements 130, 140, and 150, by analogy with those in FIG. 1A) and is represented by surfaces 12-17, with the image formed at the retina (surface 18). The corneal surfaces are denoted 12 and 13, the front surface of the eye-lens is 15 and the back surface of the eye-lens is surface 16. The retina of the eye is represented, in this example, by a hemispherical surface of a radius with absolute value of 12 mm. Various aberrations are evaluated on that spherical surface 18 (which is the reason why the raytracing is performed from the camera sensor, surface 1, to the eye).

(A skilled optical designer will understand that optical several surfaces not identified in FIG. 3A by a single-digit or a double-digit numeral-for example, surface 2—were used as dummy surfaces simplifying the ZEMAX model set-up. Surface 2 is substantially in contact with surface 1.)

Notably, all optical surfaces of the embodiment 300 are "standard" surfaces (in terminology used in Zemax), which are conic surfaces (the description of which contains no aspheric terms other than a specified conic constant). In the case of spherical surfaces, the conic constant is zero (the value is left blank/empty in Table 3).

When mechanically-cooperated with the lens of the mobile device at a separation of about 23 mm from the lens of the mobile device, the telescope 300 of the invention is configured for straightforward imaging of the posterior surface of the eye (for example, fundus) just as the embodiment 100, but with a substantially smaller chromatic aberrations, due to the achromatic doublet nature of constituent lenses 310, 320.

It is understood, therefore, that the embodiment 300 (by analogy with the embodiment 100) provides a relay optical system including first and second positive lenses. The first lens has a biconvex shape and first and second surfaces that have, respectively, first and second surface curvatures (the first surface curvature being larger than the second surface curvature). The second lens is also dimensioned in a biconvex fashion and has third and fourth surfaces (that have, respectively, third and fourth surface curvatures, the third surface curvature being larger than the fourth surface curvature). The first and second lenses are mutually oriented to have the first and third surfaces face one another. The first and second lenses may be formatted to be substantially identical to one another to form a symmetrical optical system characterized by unit magnification. In general, each of the first and second lenses may be dimensioned to satisfy the condition of $0.2<|Q|<0.8$, where $|Q|=(R_b+R_a)/(R_b-R_a)$. Here, $R_a$ represents the larger radius of curvature between the radii of curvature of the two surfaces of a given lens, and $R_b$ represents the smaller radius of curvature between the radii of curvature of the two surfaces of such given lens.

As seen from FIG. 3A and Table 3, the design 300 employs one conic aspheric surface for each of the constituent ophthalmic lenses 310, 320.

TABLE 3

SURFACE DATA SUMMARY for Embodiment of FIG. 3A:

| Surface | Type | Radius | Thickness | Glass Nd | Vd | Clear Diameter | Conic Constant |
|---|---|---|---|---|---|---|---|
| 0 (OBJ) | STANDARD | Infinity | 3.9 | | | 3.6 | |
| 1 (STOP) | PARAXIAL | Infinity | 0 | | | 2 | |
| 2 | STANDARD | Infinity | 23 | | | 2.1 | |
| 3 | STANDARD | 127.787 | 2 | 1.8081 | 22.761 | 24.92783 | |
| 4 | STANDARD | 22.07903 | 10 | 1.8160 | 46.621 | 27.20494 | |
| 5 | STANDARD | −27.23377 | 0 | | | 28.21082 | −1.598561 |
| 6 | STANDARD | Infinity | 27.06517 | | | 27.99629 | |
| 7 | STANDARD | Infinity | 26.9117 | | | 26.47767 | |
| 8 | STANDARD | 27.23377 | 10 | 1.8160 | 46.621 | 28.44318 | −1.598561 |
| 9 | STANDARD | −22.07903 | 2 | 1.8081 | 22.761 | 27.47527 | |
| 10 | STANDARD | −127.787 | 17.91428 | | | 25.25478 | |
| 11 | STANDARD | Infinity | 2.09 | | | 7.425611 | |
| 12 | STANDARD | 7.72 | 0.95 | 1.3792 | 61.513 | 5.042444 | −0.26 |
| 13 | STANDARD | 6.5 | 3.05 | 1.3370 | 52.659 | 4.56261 | |
| 14 | STANDARD | Infinity | 0.0001 | 1.3370 | 52.659 | 2.189268 | |
| 15 | STANDARD | 10.2 | 4 | 1.4200 | 51.226 | 2.143762 | |
| 16 | STANDARD | −6 | 4.32 | 1.3360 | 53.342 | 4.306516 | −1 |
| 17 | STANDARD | Infinity | 12 | 1.3360 | 53.342 | 7.380894 | |
| 18 (IMA) | STANDARD | −12 | | 1.3360 | 53.342 | 24 | |

Figure 3B:
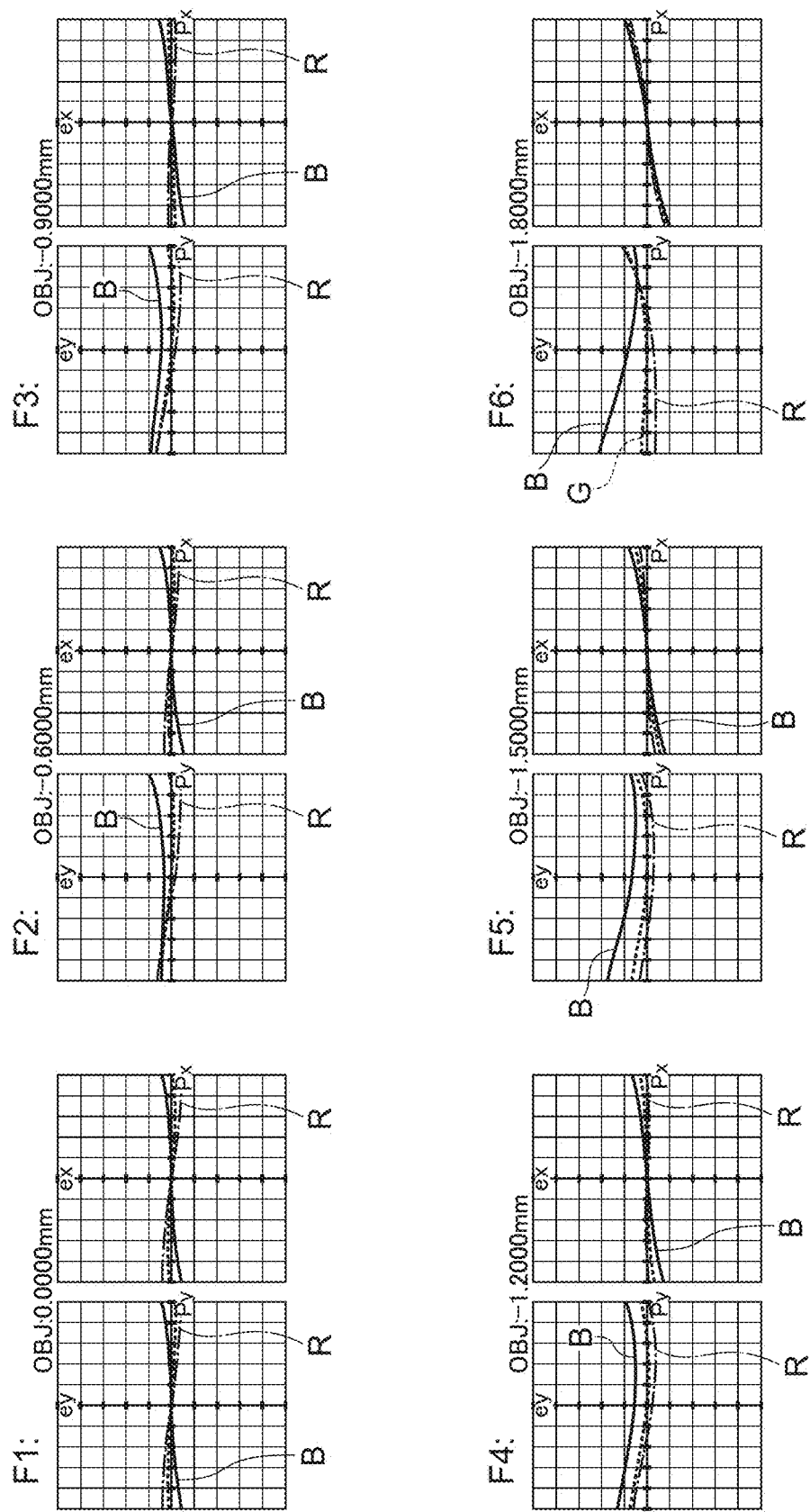
FIG. 3B displays six combinations (F1, F2, F3, F4, F5, and F6) of two plots each. These combinations represent ray aberrations on the retinal surface across the 50 degree field-of-view for six given values of the height of the object, at chosen wavelengths of the imaging spectrum (R=0.656 microns; G=0.588 microns; B=0.486 microns), both along the y- and x-axes of the local coordinate system.

FIG. 3B displays the transverse ray fan plots at the image surface (denoted as IMA in FIG. 3A), representing primarily axial color aberrations (that is, a chromatic variation of position of a focal point). Here, the maximum scale for each of the plots is +/−100 microns. The ray fan plots are presented for different heights of the object (that is, for different object fields numbered F1, F2, . . . , F6, where the absolute value of the height of the object point in field F1 is chosen to be zero, in F2: 0.6 mm, and in the largest field F6: 1.8 mm). Maximum scale of each ray fan plot here is +/−100 microns.

Figure 3C:
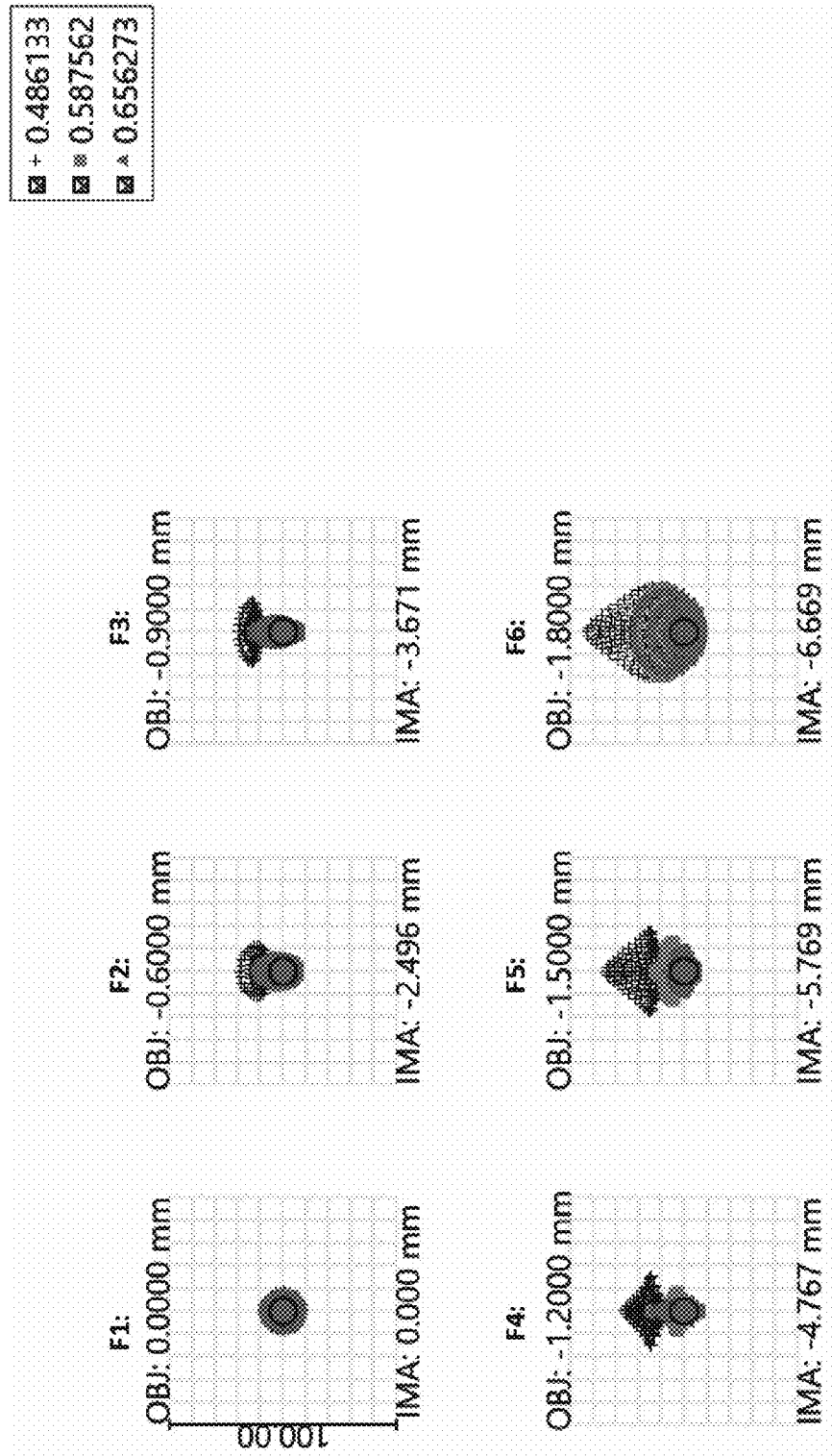
FIG. 3C contains spot diagrams corresponding to those locations at the image surface, across the 50 degree field-of-view, which are defined by imaging of the object points at the six given values of the height of the object (F1, F2, . . . , F6, corresponding to those of FIG. 3B)

FIG. 3C characterizes the imaging performance of the embodiment 300 and shows the spot diagrams in the image surface for the same object fields numbered F1, F2, . . . , F6. The Airy radius is 5.916 µm. The rms radii of the spot diagrams at the image surface, corresponding to imaging of the object points representing these object fields are 5.391 µm, 7.847 µm, 9.609 µm, 11.243 µm, 13.142 µm, and 16.922 µm, respectively. Scale bar: 100 microns.

Example 5: Transformation of Full-Length System 300 to Image a Chosen First Anterior Surface of the Eye The operational advantage of the embodiment 300 of the invention manifests in the fact that that embodiment is easily transformable, changeable into a simplified version that is immediately adopted, in conjunction with the imaging system of the same auxiliary device (such as the cell phone, for example) for imaging a different ophthalmic surface. The transformation of the embodiment 300 is rather trivial, and stems from removing a lens that is distal to the auxiliary device (in reference to FIG. 3A-removing the lens 320). A skilled person will appreciated that, as a result of such transformation, the substantially-symmetric telescopic system 300 is turned into what may be classified as an optical magnifier.

Figure 4A:
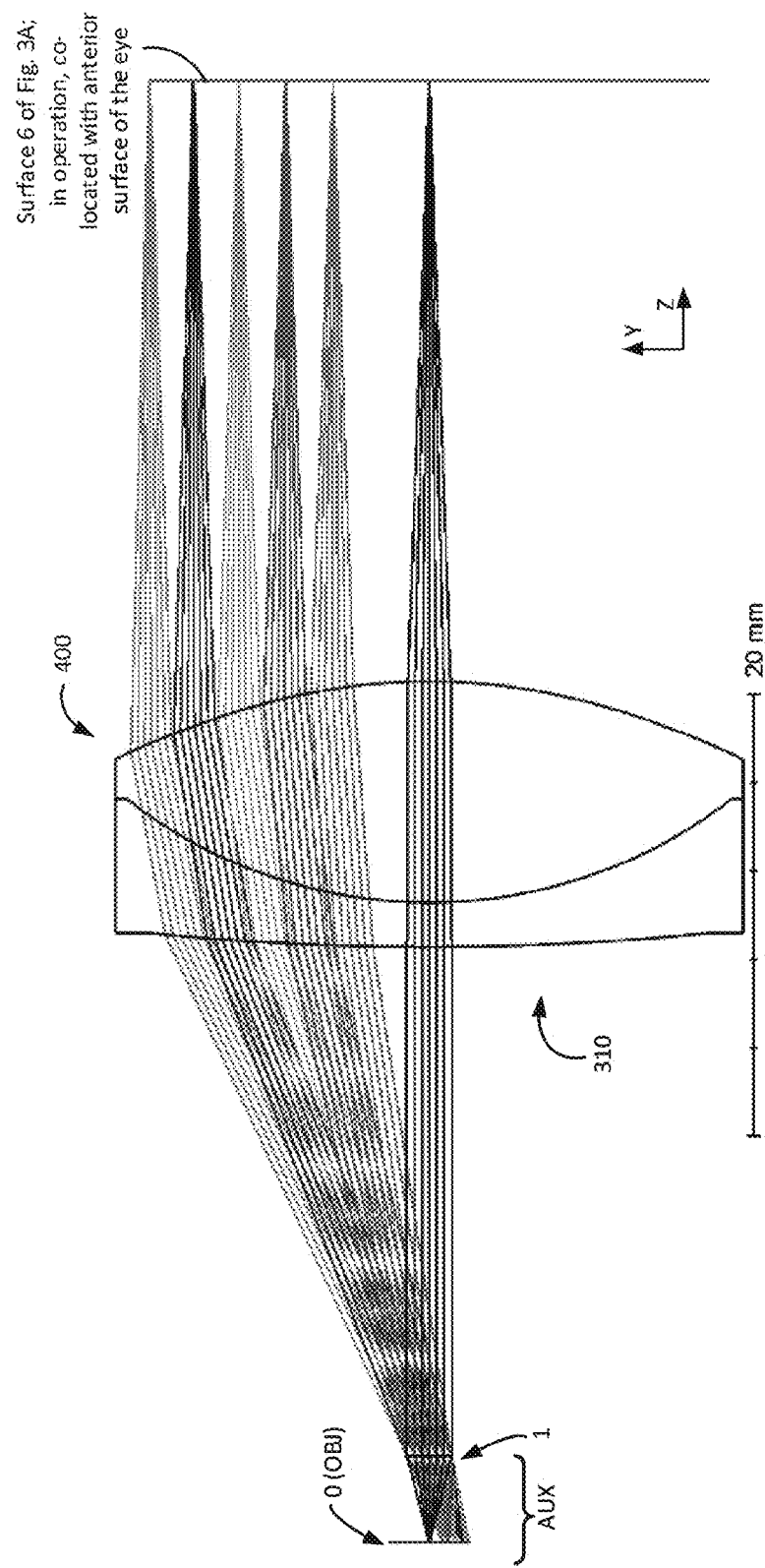
FIG. 4A schematically illustrates the structural cooperation of a transformed embodiment 400 of the invention (which represents the first half of the embodiment of FIG. 3A) with the wide-angle imaging system of the mobile device. The optical axis of the system corresponds to the z-axis of the local coordinate system.

To this end, FIG. 4A schematically illustrates the structural cooperation of a transformed embodiment 400 of the invention (which represents the first half of the embodiment of FIG. 3A) with the wide-angle imaging system of the mobile device. The optical axis of the system corresponds to the z-axis of the local coordinate system. The prescription for the optical train of the imaging system 400 of FIG. 4A and Table 4A represents and corresponds to the first half of the system 300 (comprising the optical surfaces from the object OBJ, representing an imaging sensor of an imaging camera, to and including that representing the intermediate image surface 6 of FIG. 3A). Such half-system is formed when the second lens 320 of the system 300 is removed from the embodiment 300. As a result of such transformation, the surface 6 of FIG. 3A becomes the ophthalmological (eye) surface 410 that is located in front of the retinal surface 18 and that is now subject to imaging with the embodiment 400 through the objective lens (represented by 1) of the imaging camera of a mobile device onto the surface of the imaging sensor (represented by O, OBJ) of the mobile device. The total axial length is about 65.97 mm. In one example, the ophthalmological surface 410 is a surface substantially in contact with the anterior surface of the cornea, and has a diameter of about 24 mm. The FOV of the embodiment 400 is about 50 degrees and this is large enough to cover the whole front of the eye. The total length is about 65.96 mm.

FIG. 4B displays six combinations (F1, F2, F3, F4, F5, and F6) of two plots each. These combinations represent ray aberrations on the surface 6 of FIG. 4A (corresponding to surface 6 of FIG. 4A) across the 50 degree field-of-view for six given values of the height of the object, at chosen wavelengths of the imaging spectrum (R=0.656 microns; G=0.588 microns; B=0.486 microns), both along the y- and x-axes of the local coordinate system. The Airy radius is 10.14 µm. The rms radii of the spot diagrams at the image surface, corresponding to imaging of the object points representing these object fields are 0.960 μm, 8.278 μm, 9.731 μm, 10.071 μm, 19.108 μm, and 48.041 μm, respectively. Scale bar: 100 microns.

FIG. 4C contains spot diagrams corresponding to those locations at the surface 6, across the 50 degree field-of-view, which are defined by imaging of the object points at the six given values of the height of the object (F1, F2, . . . , F6, corresponding to those of FIG. 4B).

It is appreciated, therefore, that as a result of a simple transformation from the embodiment 300 of the fundus camera to the embodiment 400 of the optical magnifier, an additional degree of operational freedom has been gained-specifically, to image yet another ophthalmological surface (of the eye) in addition to the retinal surface with the same imaging system of the same auxiliary (external to the embodiments of the invention, for example, mobile) device as that used with the embodiment 400.

camera lens of the mobile device to the second camera lens of the mobile device—the transformed embodiment 400 can be employed for imaging of yet another anterior surface of the eye, the angular extent of which approximately corresponds to the FOV of the second camera lens of the auxiliary device.

Figure 4D:
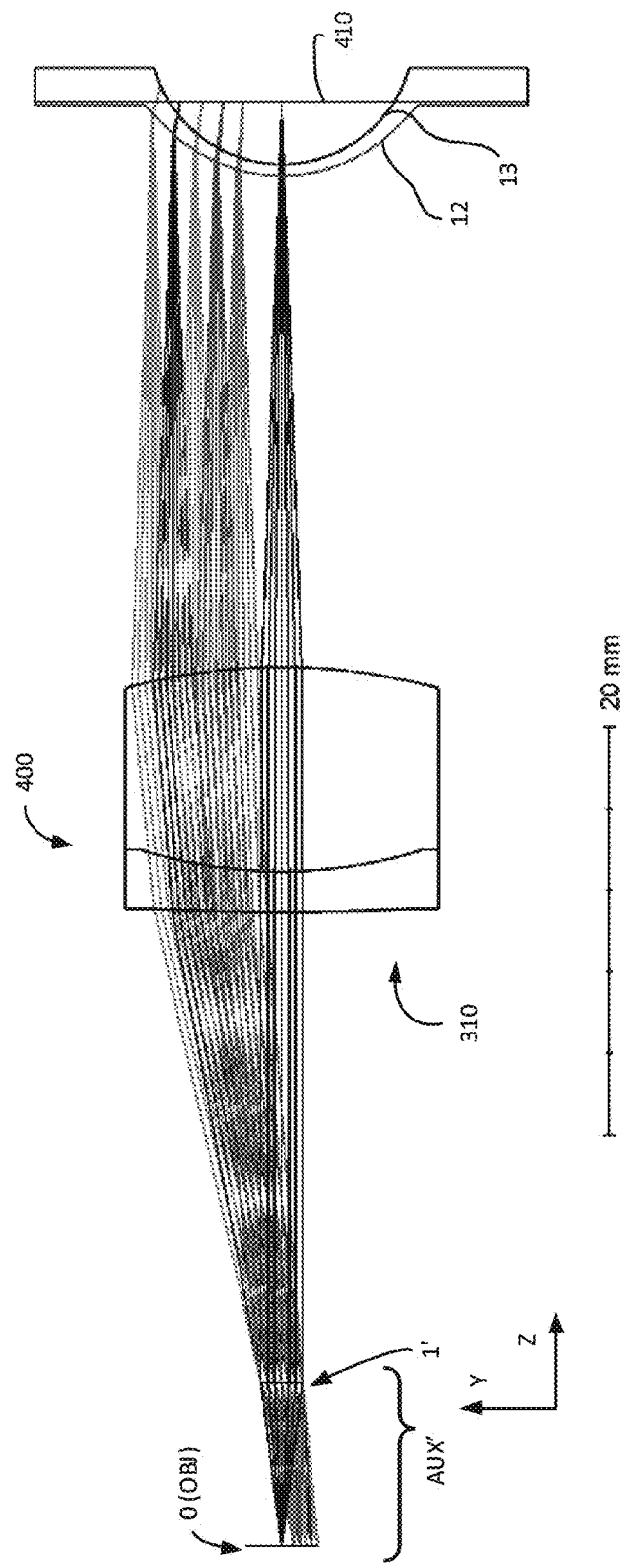
FIG. 4D schematically illustrates the structural cooperation of the transformed embodiment of FIG. 4A, which represents the first half of the embodiment of FIG. 3A, with the narrow-angle imaging system of the mobile device. The optical axis of the system corresponds to the z-axis of the local coordinate system.
Figure 4F:
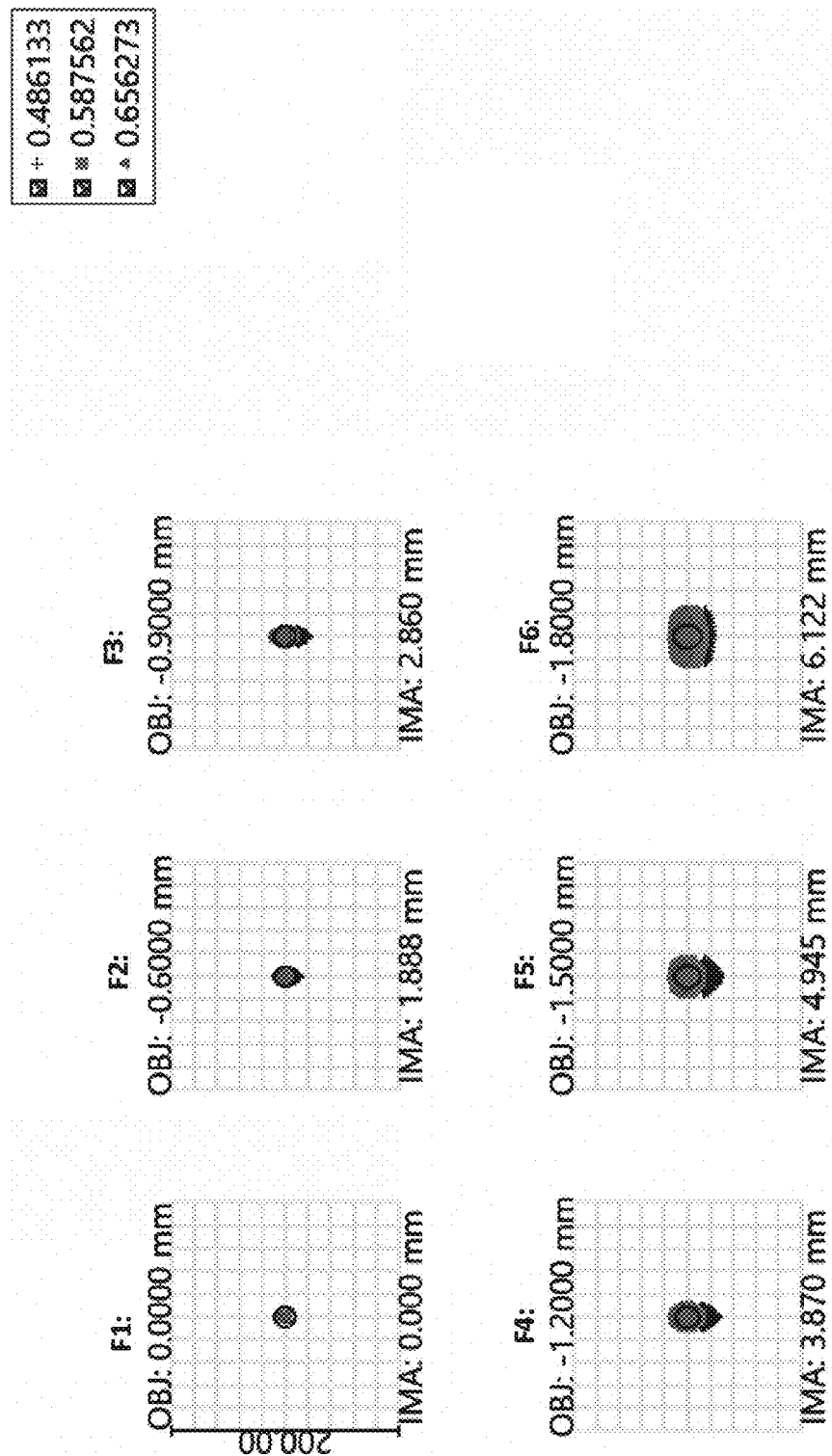
FIG. 4F contains spot diagrams corresponding to those locations at the surface 9 (IMA), across the 25 degree field-of-view, which are defined by imaging of the object points at the six given values of the height of the object (F1, F2, . . . , F6, corresponding to those of FIG. 4E)

An example of such use is represented by FIGS. 4D, 4E, 4F and Table 4B. In this narrow-angle case (FOV ~25 degrees), the combination of the narrow-angle camera lens of the mobile device and the embodiment 400 is configured to image another anterior surface of the eye (the one different from the corneal surface)—for example, the surface of the eye's iris that is immersed in aqueous humor.

Here, FIG. 4D schematically illustrates the structural cooperation of the transformed embodiment 400 of FIG. 4A (which represents the first half of the embodiment of FIG. 4A) with the narrow-angle imaging system of the auxiliary mobile device. The optical axis of the system corresponds to

TABLE 4A

SURFACE DATA SUMMARY: Cooperation of a Wide-Angle Lens with Embodiment 400:

| Surface | Type | Radius | Thickness | Glass Nd | Vd | Clear Diameter | Conic Constant |
|---|---|---|---|---|---|---|---|
| 0 (OBJ) | STANDARD | Infinity | 3.9 | | | 3.6 | |
| 1 (STOP) | PARAXIAL | Infinity | 0 | | | 2 | |
| 2 | STANDARD | Infinity | 23 | | | 2.1 | |
| 3 | STANDARD | 127.787 | 2 | 1.8091 | 22.761 | 24.92783 | |
| 4 | STANDARD | 22.07903 | 10 | 1.8160 | 46.621 | 27.20494 | |
| 5 | STANDARD | −27.23377 | 0 | | | 28.21082 | −1.598561 |
| 6 | STANDARD | Infinity | 27.06917 | | | 27.99629 | |
| IMAGE | STANDARD | Infinty | | | | 25.21683 | |

TABLE 4B

SURFACE DATA SUMMARY: Cooperation of a Narrow-Angle Lens with Embodiment 400:

| Surface | Type | Radius | Thickness | Glass Nd | Vd | Clear Diameter | Conic Constant |
|---|---|---|---|---|---|---|---|
| 0 (OBJ) | STANDARD | Infinity | 3.9 | | | 3.6 | |
| 1 (STOP) | PARAXIAL | Infinity | 0 | | | 2 | |
| 2 | STANDARD | Infinity | 23 | | | 2.1 | |
| 3 | STANDARD | 127.787 | 2 | 1.8081 | 22.763 | 13.01881 | |
| 4 | STANDARD | 22.07903 | 10 | 1.8160 | 46.621 | 13.63563 | |
| 5 | STANDARD | −27.23377 | 0 | | | 15.29172 | −1.598561 |
| 6 | STANDARD | Infinity | 24 | | | 15.22123 | |
| 7 | STANDARD | 7.72 | 0.55 | 1.3752 | 31.513 | 13.2767 | −0.26 |
| 8 | STANDARD | 6.5 | 3.05 | 1.3370 | 52.659 | 12.48791 | |
| 9 | STANDARD | Infinity | 0.0001 | 1.3370 | 52.659 | 12.87573 | |
| IMAGE | STANDARD | Infinity | | 1.3360 | 53.342 | 11.0 | |

Example 6: Transformation of the Gull-Length System 300 to Image a Second Anterior Surface of the Eye Notably, the embodiment 300 of the invention transformed as a result of removing the lens 320 can also be used in a situation when the imaging system of the auxiliary device is a dual-imaging system—for example, when in addition to the wide-angle lens the mobile device such as the cell-phone is equipped with a second, narrow-angle camera lens. In this case- and assuming that the connector between the embodiment of the optical system of the invention and the mobile device is equipped with some sort of a translational stage configured to relatively reposition the optical system of the embodiment of the invention from the first the z-axis of the local coordinate system. In reference to FIG. 4D and Table 4B, the stop, or pupil, surface 1' (also denoted as STOP), represents the narrow-angle lens of the cellphone camera, which is in Zemax described as a zero-aberration paraxial lens, disposed at a distance of about 8.0 mm from the camera's imaging sensor that is denoted as surface 0 or OBJ. (The separation between the surfaces 0 and 1' is substantially equal to the focal length of the typical narrow-angle cellphone camera lens, which in these calculations is assumed to be a perfect lens.) Accordingly, the combination of optical elements 0 and 1', denoted as AUX' in FIG. 4D, represents the imaging system of the device that is auxiliary, external to the embodiment 400 (such as a mobile device, cellphone in particular). The total axial length is about 70.6 mm. A skilled artisan will appreciate that some of the surfaces described in Table 2B are dummy surfaces used for the purposes of efficient set-up of the ZEMAX design model, as commonly used in the art. The diameter of the image field (at surface IMA) is 11 mm, which is large enough to cover most of the fully-dilated iris.

FIG. 4E complements the description of the use of the transformed embodiment of the invention with the narrow-angle imaging lens of the mobile device by displaying six combinations (F1, F2, F3, F4, F5, and F6) of two plots each. Maximum scale is +/−200 microns. These combinations represent ray aberrations on the surface (IMA) of FIG. 4D across the approximate 25 degree field-of-view for six given values of the height of the object, at chosen wavelengths of the imaging spectrum (R=0.656 microns; G=0.588 microns; B=0.486 microns), both along the y- and x-axes of the local coordinate system.

Finally, FIG. 4F contains spot diagrams corresponding to those locations at the surface (IMA), across the 25 degree field-of-view, which are defined by imaging of the object points at the six given values of the height of the object (F1, F2, ..., F6, corresponding to those of FIG. 4E). The Airy radius is 8.959 µm. The rms radii of the spot diagrams at the image surface, corresponding to imaging of the object points representing these object fields are 00.477 µm, 5.678 µm, 8.601 µm, 11.214 µm, 13.341 µm, and 15.702 µm, respectively. Scale bar: 100 microns.

Overall, the embodiments of the invention can be characterized as follows:

While primarily intended for imaging the anterior eye, the transformed (magnifier or loupe) version of each of the full-length embodiments has a field of view that could also be used to photograph or image not only a plurality of the different ophthalmic surfaces but also skin abnormalities such as, for example, melanoma.

Both types of embodiments—the full-length system(s) configured to image a posterior portion of the eye and a shortened (or transformed) system(s) configured for imaging on an anterior portion of the system can use the illuminator system equipped with a polarizing beamsplitter and analyser in between the camera and first ophthalmic lens, and an array of LED's, which could include a programable micro-LED array.

Embodiments of the invention provide

1. Very low-cost, compact fundus imaging camera that is convertible or transformable to a very low-cost, compact, anterior eye camera.

2. Embodiments of the invention facilitate imaging a larger portion of the retina with multiple exposures and image-stitching.

3. The designs taking into account the juxtaposition of the embodiments of the invention with a dual-lens cellphone imaging camera provides further flexibility in field-of-view of the imaging process.

The system could be applied to extremely low-cost, fundus and anterior chamber camera, replacing more expensive slit lamps and fundus cameras or opening new markets in countries that cannot afford expensive ophthalmic equipment, while providing a permanent image record and application to telemedicine.

Figure 5:
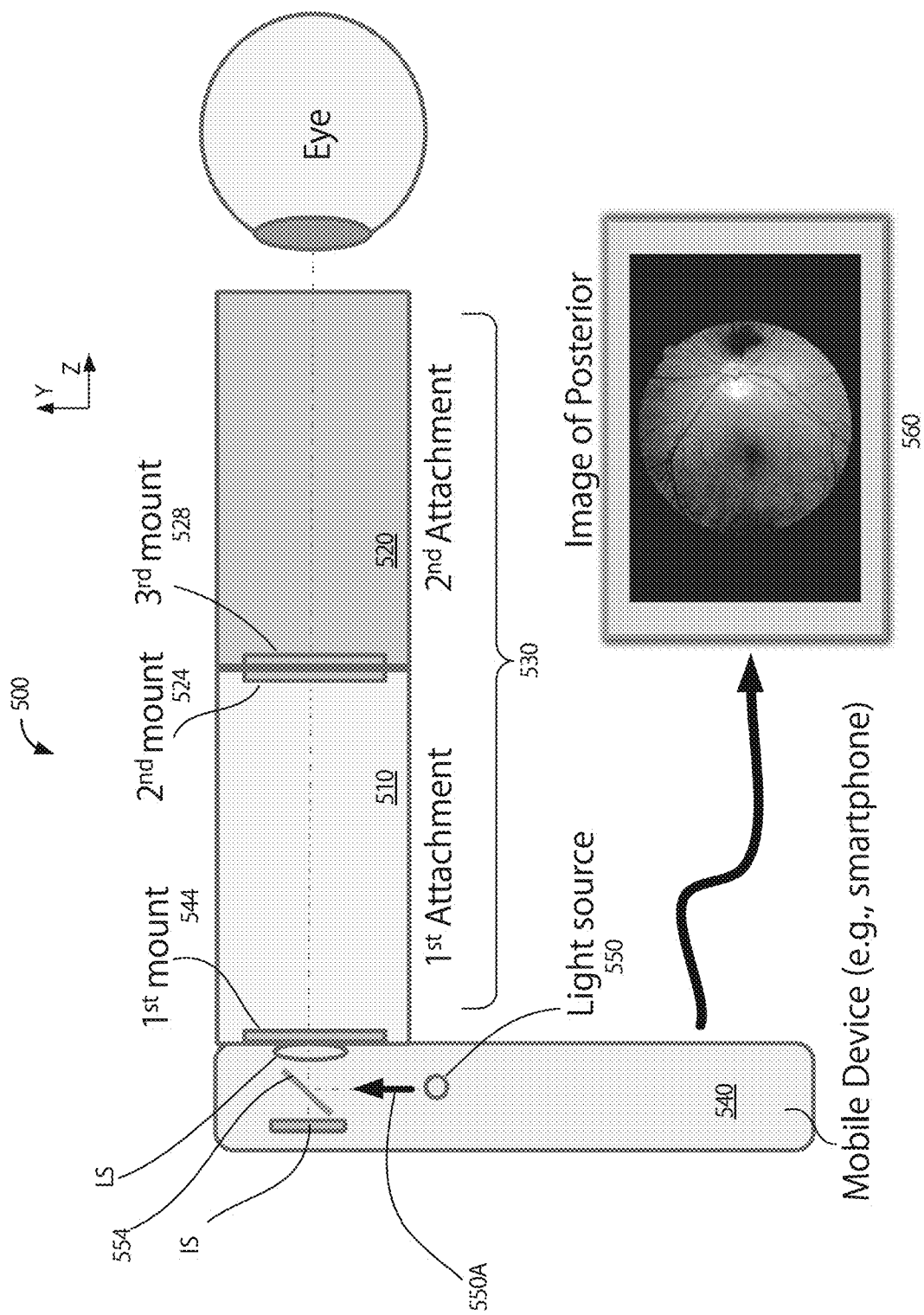
FIG. 5 is a schematic of the overall imaging system configured to image a posterior ophthalmic surface.

The transformation of the overall imaging system from the version configured to image a posterior surface of the eye to the surface configured to image an anterior surface of the eye (and vice versa) will be easily appreciated from FIGS. 5 and 6.

Here, FIG. 5 provides a schematic diagram 500 of a tangible structure of an embodiment of the overall imaging system containing the optics discussed in reference to FIGS. 1A and 3A. As shown, the sequence of two mechanical attachments 510, 520 (each, in one implementation, configured as a tubular section or member carrying within it and supporting a respectively-corresponding optic element 110 or 310, and 120 or 320) that are removably affixed to one another co-axially with the use of the mounting elements 524, 528. (Generally, the tubular members may be enclosing—in addition to the two optical elements possessing non-zero optical powers—additional optics such as, for example, windows configured to seal the tubular member and/or optical filters. It is understood, therefore, that in one case a given tubular member includes only a corresponding lens and is devoid of an additional optical element that possesses a substantially non-zero optical power.)

The overall sequence or combination 530 of the mechanical attachments 510, 520 is in turn removably and repositionally affixed to the housing of the mobile device 540 such as to position the optical relay (defined by the combination of the lenses 110 and 120 or the combination of the lenses 310 and 320, depending on the embodiment, each of which combinations is configured as an afocal relay) coaxially with the optical system of the mobile device containing at least one lens LS, and in accord with the design prescription of Table 1 or Table 3, respectively. The optical lenses are not shown for simplicity of illustration. From the above-presented discussion it is understood that the optical system of the mobile device may include two lenses: a wide-angle lens and a narrow-angle lens. The removable and repositionable attachment between the overall externa-to-the-mobile-device combination 530 and the mobile device is effectuated with the use of yet another mount 544, which generally may incorporate a spatial repositioning device such as a mechanical translation stage in order to transversely (that is, in xy-plane) and reversibly move or reposition the combination 530 from one lens of the device 540 to another (when two lenses are present in the mobile device). The repositioning device is not shown for simplicity of illustration. Generally, at least one of the mounting elements 524, 528, 544 may include at least one of a mechanical contraptions (such as a thread or a snap-clip, for example) or an appropriate magnetic lock, to name just a few.

The mobile device 540 of the embodiment 500 may additionally include an internal source of light (such as semiconductor laser), which, in operation, delivers the light output in reflection from the beamsplitter 554 through the optics of the relay system (housed in the article of manufacture 530) towards the eye when the afocal (optical relay) housed in the attachment combination 530 is appropriately spatially-coordinated with the position of the eye pupil in order to define an optically-conjugate relationship between the pupil of the subject's eye and the pupil of the external optical system LS.

The optical relay system housed in the article of manufacture 530 then collects the light reflected from a target ophthalmic surface of the eye and delivers it through the beamsplitter 554 to the imaging sensor IS. The programmable processor of the mobile device (not shown here for simplicity of illustration) acquired the data output representing the image of the target ophthalmic surface from the sensor IS and, in one embodiment, transmits these data with the use of an appropriate electronic circuitry to an auxiliary device judiciously configured to generate a visual representation (for example, in a form of a displayed image) of the target surface of the eye to the user. (In a related implementation, the programmable processor of the mobile device may be appropriately programmed to display the image on the monitor/display of the mobile device 540.) The insert to FIG. 5 illustrates the example 560 of the posterior ophthalmic surface of the eye (such as the image of the retina) formed with the use of the system 500.

In order to structurally implement reconfiguration (or transformation) from the imaging optical system configured according to embodiments 100, 300 to the one configured according to embodiments 200, 400, the overall system 500 has to be accordingly restructured. To this end, FIG. 6 illustrates the structure 600 (which represents the structure 500 modified by removing the tubular attachment 520 (that is proximal to the eye and distal to the imaging sensor IS of the mobile device 540) with the lens 120 or 320 contained in it, leaving only the proximal-to-the-device-540 portion 544 of the lens housing with the lens 110 (or 310) carried in it. After the system 600 has been reversibly formed from the system 500, and after the system has been appropriately positioned with respect to the eye such as to define an optically-conjugate relationship between the pupil of the subject's eye and the pupil of the external optical system LS, the system 600 is operated as discussed above in reference to FIG. 5, to produce a visually-perceivable representation 650 of the anterior ophthalmic surface of the eye. (The transformation from the system 600 to the system 500 is carried out in reverse—that is, by attaching the tubular housing portion 520 with the respectively-corresponding lens contained in it to the portion 510.)

FIG. 7 schematically illustrates a portion of the process of imaging a section of a visual system of a subject. At the initiation stage, the invention of the imaging system of the invention is set into a state of image acquisition. The initiation stage includes at least step 710 (during which the program code loaded onto the programmable processor of the system of the invention or on the processor of the external controller that is configured to govern the operation of the system of the invention activates the operation of the system), and step 714 (during which the mode of image acquisition is chosen—that is, the mode of imaging an anterior portion of the eye or the mode of imaging a posterior portion of the eye, or a hybrid mode: anterior and posterior portions).

For acquisition of the image of only the anterior portion of the eye, the controller then instructs the system to confirm, at step 718, whether the proximal attachment 510 with housed—therein optics is mounted to the hosting mobile device 540 to complement the imaging lens LS with the lens 110 or 310 (depending on the implementation of the optical system of the attachment 510). The affirmative confirmation is followed by the step 722 of aligning the imaging system with respect to and focusing it on the target anterior portion of the eye, and the step 726 of acquisition of imaging data and appropriately storing such data on a non-transient, tangible storage memory. The controller further queries the user whether the additional imaging of a target posterior portion of the eye is required, at step 730, and, depending on the decision, passes the process either to the (optional) step of processing the anterior imaging data, 736, or to the sequence of steps 742, 756, 760 associated with the imaging of the posterior portion of the eye.

If the imaging mode was chosen, at the step 714, to be the mode of imaging of the posterior portion of the eye, the imaging process proceeds through steps 748, 752 at which the system confirms that both the proximal and distal optical attachments (510, 520 in FIGS. 5, 6) are appropriately mounted to the hosting mobile device 540 to complement the imaging lens LS with lenses 110 (or 310) and 120 (or 510), depending on the implementation of the optical system of the combination 530 of the attachments. The imaging of the posterior target portion of the eye then is effectuated by aligning and focusing the overall optical system with respect to the target portion of the eye, 756; acquisition of the posterior portion imaging data, 756; and appropriate storing such imaging data at the tangible memory storage. A person of skill in the art will readily appreciate that image processing of any of the acquired anterior portion image data and posterior portion image data (steps 736, 766) is generally optional, and may be carried out when so decided by the user to produce a required image output (such as, for example, a tangible visually-perceivable representation of the anterior and/or posterior portions of the eye 660, 560—for example, on an appropriate display to which the imaging system is operably connected, optionally wirelessly).

Embodiments of the techniques described in the present disclosure may include any number of the following aspects, either alone or combination:

1. A method for imaging a posterior surface and an anterior surface of an eye, the method comprising:
   forming a first posterior image of the posterior surface with a first combination of an afocal optical relay and a first lens system that is built into a telecommunication device, the first lens system having a first optical axis,
   wherein the afocal optical relay i) includes first and second lenses that possess equal optical characteristics and ii) has an unity optical magnification;
   transforming the afocal optical relay to a loupe by removing one of the first and second lenses without mutual repositioning of the first lens system and the other of the first and second lenses with respect to one another along the first optical axis; and
   forming a first anterior image of the anterior surface with a second combination of the loupe and the first lens system.

2. The method according to aspect 1,
   wherein said forming the first posterior image includes forming an image of a fundus of the eye, and
   wherein said forming the first anterior image includes forming an image of at least one of an iris of the eye, a sclera of the eye, and a surface of or within a crystalline lens of the eye.

3. The method according to aspect 1, further comprising:
   adding the one of the first and second lenses to the loupe to form the afocal relay and without repositioning of the first lens system and the other of the first and second lenses with respect to one another along the first optical axis.

4. The method according to aspect 1, further comprising at least one of the following:
   a) repositioning the afocal relay and the first telecommunication device relative to one another in a direction transverse to the first optical axis until a second optical axis of a second lens system substantially coincides with an optical axis of the other of the first and second lenses; and
   forming a second posterior image of the posterior surface of the eye;
   and
   b) repositioning the loupe and the first telecommunication device relative to one another in said direction until the second optical axis substantially coincides with the optical axis of the other of the first and second lenses; and
   forming a second anterior image of the anterior surface of the eye.

5. The method according to aspect 4,
wherein said forming the second posterior image includes forming an image of the of the eye, and
wherein said forming the first anterior image includes forming an image of at least one of the iris of the eye, the sclera of the eye, and the surface of or within the crystalline lens of the eye.

6. The method according to aspect 1, wherein said afocal optical relay includes only the first and second lenses and does not include any other optical element that has a substantially non-zero optical power.

7. The method according to aspect 1, wherein said forming the first posterior image includes transmitting light from a fundus of the eye through a combination of the first and second lenses positioned so as to have mutually-spatially-congruent surfaces of the two lens elements face each other.

8. The method according to aspect 1, wherein each of the first and second lenses represents a single, stand-alone lens element.

9. The method according to aspect 1, wherein each of the first and second lenses represents an optical doublet.

10. The method according to aspect 1, wherein the afocal relay has a full-angle field-of-view (FOV) that is substantially equal to 50 degrees.

11. The method according to aspect 1, wherein the loupe has a full-diameter FOV that is substantially equal to 12.5 mm.

The invention claimed is:

1. A relay optical device configured, in combination with an external optical device, to interchangeably image a posterior part of a subject's eye and an anterior part of the subject eye, the relay optical device comprising;
a first tubular member having a first lens with a first positive optical power supported therein, a first mount, and a second mount, the first tubular member being detachably attached to the external optical device via the first mount; and
a second tubular member having a second lens with a second positive optical power supported therein and a third mount, wherein
the second tubular member is coaxially and detachably mounted to the first tubular member by engaging the third mount with the second mount to optically relay a pupil of the subject's eye to a pupil of an external optical system through the combination of the first and second lenses,
the first and second lenses of the combination form an afocal optical system configured to transfer an image of the posterior part of the subject's eye to the external optical device, and
when the second tubular member is removed from the first tubular member, the first lens is configured to transfer an image of the anterior part of the subject's eye to the external optical device.

2. A relay optical device of claim 1, further comprising:
a control device configured to monitor a condition as to whether the second tubular member is coaxially affixed to the first tubular member, to generate a discriminating signal representing whether a first image of the posterior part of the eye is being formed through the combination of the first and second lenses or a second image of the anterior part of the eye is being formed through only the first lens, and
to send said discriminating signal to the external optical device.

3. The relay optical device of claim 1, wherein:
the first and second lenses possess equal optical properties, the afocal optical system configured to have a unity magnification and to provide diffraction-limited imaging within a spectral range from at least 486 nm to at least 656 nm.

4. The relay optical device of claim 1, wherein:
each of the first and second lenses of the afocal optical system is configured as an optical doublet.

5. The relay optical device of claim 1, wherein:
each of the first and second lenses of the afocal optical system is configured as a single, stand-alone lens element.

6. The relay optical device of claim 1, wherein:
the first lens has a biconvex shape and first and second surfaces having respectively-corresponding first and second surface curvatures, the first surface curvature being larger than the second surface curvature;
the second lens has the biconvex shape and third and fourth surfaces having respectively-corresponding third and fourth surface curvatures, the third surface curvature being larger than the fourth surface curvature; and
the first and second lenses are mutually oriented to have the first and third surfaces face one another.

* * * * *